(12) United States Patent
Armitage et al.

(10) Patent No.: US 11,124,822 B2
(45) Date of Patent: Sep. 21, 2021

(54) ENHANCED BIOMOLECULE DETECTION ASSAYS BASED ON TYRAMIDE SIGNAL AMPLIFICATION AND GAMMAPNA PROBES

(71) Applicant: CARNEGIE MELLON UNIVERSITY, Pittsburgh, PA (US)

(72) Inventors: Bruce Alan Armitage, Pittsburgh, PA (US); Veronica Hinman, Pittsburgh, PA (US); Munira F. Fouz, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 122 days.

(21) Appl. No.: 15/518,811

(22) PCT Filed: Oct. 16, 2015

(86) PCT No.: PCT/US2015/055949
§ 371 (c)(1),
(2) Date: Apr. 13, 2017

(87) PCT Pub. No.: WO2016/061460
PCT Pub. Date: Apr. 21, 2016

(65) Prior Publication Data
US 2017/0226572 A1   Aug. 10, 2017

Related U.S. Application Data

(60) Provisional application No. 62/122,347, filed on Oct. 17, 2014.

(51) Int. Cl.
| | | |
|---|---|---|
| C12Q 1/6841 | (2018.01) | |
| C12Q 1/682 | (2018.01) | |
| C12Q 1/6816 | (2018.01) | |
| C12Q 1/6818 | (2018.01) | |

(52) U.S. Cl.
CPC ........... *C12Q 1/6841* (2013.01); *C12Q 1/682* (2013.01); *C12Q 1/6816* (2013.01); *C12Q 1/6818* (2013.01)

(58) Field of Classification Search
None
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 5,496,938 A | 3/1996 | Gold et al. |
| 5,567,588 A | 10/1996 | Gold et al. |
| 5,580,737 A | 12/1996 | Polisky et al. |
| 5,637,459 A | 6/1997 | Burke et al. |
| 5,660,985 A | 8/1997 | Pieken et al. |
| 5,683,867 A | 11/1997 | Biesecker et al. |
| 5,702,892 A | 12/1997 | Mulligan-Kehoe |
| 5,707,796 A | 1/1998 | Gold et al. |
| 5,750,373 A | 5/1998 | Garrard et al. |
| 5,821,047 A | 10/1998 | Garrard et al. |
| 5,948,635 A | 9/1999 | Kay et al. |
| 6,127,132 A | 10/2000 | Breitling et al. |
| 6,248,558 B1 | 6/2001 | Lin et al. |
| 8,053,212 B1 | 11/2011 | Benner |
| 8,389,703 B1 | 3/2013 | Benner et al. |
| 8,653,254 B2 | 2/2014 | Umemoto et al. |
| 2008/0076139 A1 | 3/2008 | Singh |
| 2012/0100540 A1* | 4/2012 | Wu ........................ C12Q 1/682 435/6.11 |
| 2012/0276530 A1* | 11/2012 | Meller ................. C12Q 1/6839 435/6.11 |
| 2013/0260379 A1* | 10/2013 | Alexander ........... G01N 33/542 435/6.11 |
| 2014/0249040 A1 | 9/2014 | Wu et al. |
| 2015/0197793 A1 | 7/2015 | Armitage et al. |

FOREIGN PATENT DOCUMENTS

| | | |
|---|---|---|
| WO | 9119813 A1 | 12/1991 |
| WO | 2008128352 A1 | 10/2008 |
| WO | 2013074601 A1 | 5/2013 |
| WO | 2015172058 A1 | 11/2015 |

OTHER PUBLICATIONS

Bhabak et al., Functional Mimics of Glutathione Peroxidase: Bioinspired Synthetic Antioxidants, Accounts of Chemical Research, 2010, pp. 1408-1419, vol. 43:11.
Boder et al., Directed evolution of antibody fragments with monovalent femtomolar antigen-binding affinity, Proceedings of the National Academy of Science, 2000, pp. 10701-10705, vol. 97:20.
Collins, TAML Oxidant Activators: A New Approach to the Activation of Hydrogen Peroxide for Environmentally Significant Problems, Accounts of Chemical Research, 2002, pp. 782-790, vol. 35:9.
Day, Catalase and glutathione peroxidase mimics, Biochemical Pharmacology, 2009, pp. 285-296, vol. 77.
Derossi et al., Cell Internalization of the Third Helix of the Antennapedia Homeodomain Is Receptor-independent, The Journal of Biological Chemistry, 1996, pp. 18188-18193, vol. 271:30.
Green et al., Autonomous Functional Domains of Chemically Synthesized Human Immunodeficiency Virus Tat Trans-Activator Protein, Cell, 1988, pp. 1179-1188, vol. 55.
Hanes et al., In vitro selection and evolution of functional proteins by using ribosome display, Proceedings of the National Academy of Science, 1997, pp. 4937-4942, vol. 94.
Hanes et al., Ribosome display efficiently selects and evolves high-affinity antibodies in vitro from immune libraries, Proceedings of the National Academy of Science, 1998, pp. 14130-14135, vol. 95.

(Continued)

Primary Examiner — Katherine D Salmon
(74) Attorney, Agent, or Firm — The Webb Law Firm

(57) ABSTRACT

Provided herein are methods of detecting target analytes, such as nucleic acids, for example microRNAs using an enhanced Tyramide Signal Amplification (TSA) method that employs probes tagged with tyramide-binding groups to amplify the effects of the TSA. The accessibility of the tyramide-binding groups, such as hydroxyphenyl groups, provides for large improvements in signal due to faster reaction with the radicals. The present invention further includes the application of the assay for detecting specific microRNAs.

28 Claims, 12 Drawing Sheets

Specification includes a Sequence Listing.

(56) References Cited

OTHER PUBLICATIONS

He et al., Antibody-ribosome-mRNA (ARM) complexes as efficient selection particles for in vitro display and evolution of antibody combining sites, Nucleic Acids Research, 1997, pp. 5132-5134, vol. 25:24.
Holt et al., The use of recombinant antibodies in proteomics, Current Opinion in Biotechnology, 2000, pp. 445-449, vol. 11.
In Vitro Protein Expression Guide, PROMEGA, 2005, pp. 29-33, Chapter 6, Ribosome Display.
Marras, Selection of Fluorophore and Quencher Pairs for Fluorescent Nucleic Acid Hybridization Probes, Methods in Molecular Biology, 2006, pp. 3-16.
Montalbetti et al., Amide bond formation and peptide coupling, Tetrahedron, 2005, pp. 10827-10852, vol. 61.
Owen et al., Kuby Immunology, Seventh Edition, 2013, pp. 654-656, W.H. Freeman & Co.
Swers et al., Shuffled antibody libraries created by in vivo homologous recombination and yeast surface display, Nucleic Acids Research, 2004, pp. 1-8, vol. 32:3.
Yeast Display scFv Antibody Library User's Manual, Pacific Northwest National Laboratory, 2004, pp. 1-44, http://www.sysbio.org/dataresources/index.stm.
Yuan et al., Integrated Tyramide and Polymerization-Assisted Signal Amplification for a Highly-Sensitive Immunoassay, Analytical Chemistry, 2012, pp. 10737-10744, vol. 84.

\* cited by examiner

ENHANCED BIOMOLECULE DETECTION ASSAYS BASED ON TYRAMIDE SIGNAL AMPLIFICATION AND GAMMAPNA PROBES

CROSS REFERENCE TO RELATED APPLICATIONS

This application is a National Stage of International Patent Application No. PCT/US2015/055949, filed Oct. 16, 2015, which claims the benefit of U.S. Provisional Patent Application No. 62/122,347, filed Oct. 17, 2014, each of which is incorporated herein by reference in its entirety.

Methods and reagent kits are provided for detection of biomarkers using enhanced tyramide signal amplification (TSA).

In a typical TSA-based test, an immobilized biomolecule (e.g. protein or nucleic acid) is recognized by a specific probe, which is then secondarily recognized by an affinity reagent such as streptavidin or an antibody. The affinity reagent is conjugated to a peroxidase enzyme that catalyzes a chemical reaction resulting in the production of radicals. These radicals then form covalent bonds to the analyte as well as to the probe and/or affinity reagent. In a TSA test, the reagent that generates radicals is linked to a fluorescent dye or affinity hapten such as biotin or digoxigenin, so the reaction results in covalent deposition of multiple fluorescent dyes or haptens per analyte, leading to a signal amplification either through direct measurement of fluorescence or after addition of a fluorescent streptavidin or antibody reagent.

SUMMARY

Prior research indicates that the radicals produced during TSA react preferentially with tyrosine residues in proteins (e.g. streptavidin, antibodies). However, reliance on the limited number of sterically- and chemically-available tyramide-reactive groups in streptavidin, horseradish peroxidase (HRP), and antibodies, results in only a small signal-amplification effect. There is a need for more robust signal amplification methods.

Provided herein is a method of labeling a target analyte, such as a protein or nucleic acid. The method comprises producing a complex by selectively binding a selectivity component with the target analyte, and co-localizing a peroxidase, such as horseradish peroxidase, and a tyramide reactive moiety comprising a plurality of tyramide reactive-groups in the complex, wherein one or both of the peroxidase and the tyramide reactive moiety are linked (covalently attached) to the selectivity component. The selectivity component can be a nucleic acid or a nucleic acid analog, an antibody, a nucleic acid or nucleic acid analog ligand (e.g., an aptamer), a ligand, or any other compound or composition that binds specifically to a target analyte. The method further comprises contacting a labeled tyramide compound with the peroxidase such that the labeled tyramide compound reacts with tyramide-reactive groups of the tyramide-reactive moiety.

In one aspect, the selectivity component is a gamma peptide nucleic acid (γPNA or GammaPNA) hybridization probe bearing oligo- or polymeric phenol-containing and/or phenylborate-containing substituents, such as, but not limited to, tyrosine amino acids, hydroxyphenyl groups or phenylboronic acid, added to at least one terminus as tyramide-reactive groups of a tyramide-reactive moiety. In another aspect, a method of synthesis of that γPNA hybridization probe is provided. In a further aspect, methods of detecting hybridization of the probe, for example in situ, are provided. The accessibility of the tyramide-reactive groups, e.g. tyrosine residues compared to the context of proteins—where the tyrosine residues might be buried in the protein interior—leads to large improvements in signal due to faster reaction with tyramide radicals. The described probes are readily applicable to standard in situ hybridization methods used to detect DNA or RNA in cells, tissue or whole organisms, in addition to array or plate formats. Non-limiting examples of initial experiments done in a microtiter plate format indicate that the strategy of the methods described herein are effective.

In one specific example, a γPNA probe with six tyrosine amino acids on one terminus was compared to a γPNA probe that lacked the hexatyrosine tail, and a 10-fold increase in signal was observed for a synthetic microRNA target. Additional control experiments demonstrated good selectivity against mismatched RNA. The present invention includes the application of the assay for detecting specific microRNAs.

According to one aspect of the invention, method of identifying the presence of a target analyte in a sample is provided, comprising: (a). forming a complex of a selectivity component specific to the target analyte with the target analyte in the sample, a peroxidase, such as horseradish peroxidase, and a tag comprising a plurality of tyramide-binding groups; (b). contacting the peroxidase with labeled tyramide, forming labeled tyramide radicals, that link to the tyramide-binding groups of the tag; and (c). detecting the linkage of the label to the complex, such as by fluorescent microscopy, spectroscopy, flow cytometry, and/or imaging techniques. In one aspect, the the selectivity component is a nucleic acid or a nucleic acid analog, and binds selectively to a nucleic acid target analyte by hybridization, for example, in a further aspect, the selectivity component is a γPNA comprising residues of gamma-modified N-(2-aminoethyl)glycine monomers of the following structure:

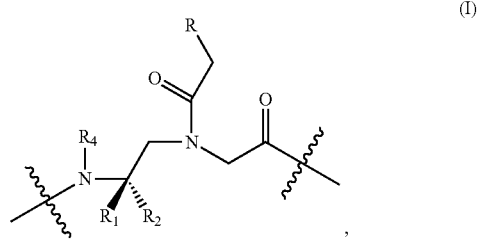

where R1, R2 and R4 are, independently, H, amino acid side chains, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, PEGylated moieties of the preceding comprising from 1 to 50 (—O—$CH_2$—$CH_2$—) residues, —$CH_2$—(O$CH_2$—$CH_2$)$_q$O$P_1$, —$CH_2$—(O$CH_2$—$CH_2$)$_q$—NH$P_1$, —$CH_2$—(O$CH_2$—$CH_2$—O)$_q$—S$P_1$ and —$CH_2$—(S$CH_2$—$CH_2$)$_q$—S$P_1$, —$CH_2$—(O$CH_2$—$CH_2$)$_q$—OH, —$CH_2$—(O$CH_2$—$CH_2$)$_q$—NH$_2$, —$CH_2$—(O$CH_2$—$CH_2$)$_r$—NHC(NH)NH$_2$, or —$CH_2$—(O$CH_2$—$CH_2$)$_r$—S—S[$CH_2$$CH_2$]$_s$NHC(NH)NH$_2$, where $P_1$ is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene; q is an integer from 0 to 10, inclusive; r and s are each independently integers from 1 to 50, inclusive, or a tyramide-binding group, such as a hydroxyphenyl group, where R1 and R2 are different, and R is a nucleobase. In one aspect, one of R1 and R2 are H. In another, at least one of R1, R2 and R4 comprise a hydroxyphenyl group. In yet another aspect, the nucleic acid or nucleic acid analog selectivity component comprises: (a). a first probe comprising a sequence complementary to a first target sequence of the nucleic acid target analyte, and a second probe complementary to a second target sequence of the nucleic acid target analyte, wherein the peroxidase is bound to the first probe and the tag is bound to the second probe; or (b). a probe comprising a sequence complementary to a target sequence of the nucleic acid target analyte and bound to the peroxidase and the tag. In another aspect, the the peroxidase or the tag is immobilized on substrate, for example, in another aspect, selectivity components having different target analyte specificities are arranged in an array, such as on a substrate, a plurality of beads, or a multiwall plate. In an in situ method, the target analyte is affixed to a microscope slide. The method is multiplexed in one aspect, by forming a second complex with a second selectivity reagent specific to a second target analyte different from the target analyte, and detecting binding of the second selectivity reagent to the second target analyte using a second labeled tyramide that can be the same as the labeled tyramide. In a further aspect, the selectivity component is a binding reagent, antibody or aptamer. In any aspect above, the tag may be a polypeptide, a PNA or a γPNA having three or more pendant tyramide-binding groups, such as hydroxyphenyl groups, for instance, in one aspect, the tag is a polypeptide of from three to 25 amino acids, comprising three or more tyrosine residues, and in another aspect, the tag is a polypeptide, a PNA or a γPNA comprising three or more tyramide-binding groups separated from each-other by at least one amino acid, PNA, or γPNA residue that does not comprise a tyramide-binding group. The target analyte can be a nucleic acid, such as a microRNA, a protein, etc.

In another aspect of the invention a kit is provided comprising, independently in one or more vessels: (a). a selectivity component specific to a target analyte bound, for example covalently, to one of a tag comprising a plurality of tyramide-binding groups or a peroxidase, (b). the other of the tag or peroxidase bound, e.g., covalently attached, to either the selectivity reagent or to a probe or a binding agent that either selectively binds the target analyte or binds to a complex formed between the selectivity component and the target analyte; and (c). a labeled tyramide, preferably labeled with a fluorophore.

In another aspect of the invention, a binding reagent for use in a tyramide signal amplification assay comprising a selectivity component covalently linked to a plurality (e.g., 2, 3, 4, 5, 6, 7, 8, 9, 10, 15, 20 or more) of tyramide-binding groups (e.g., hydroxyphenyl and/or phenylboronic acid groups). In one aspect, the selectivity component is a nucleic acid or a nucleic acid analog, and in another, the selectivity component is a peptide nucleic acid, such as a γPNA. In another aspect, the selectivity component is an antibody, an aptamer, a ligand, or an engineered polypeptide. In a further aspect tyramide-reactive group is a hydroxyphenyl group. In another, the binding reagent comprises a tyramide-reactive moiety (or tag) covalently-linked to the selectivity component. In one aspect, the tyramide-reactive moiety is a polymer comprising one or more tyramide-reactive groups. In another, the tyramide-reactive moiety is a γPNA comprising γPNA residues of from 1 to 20 residues in length and having a plurality of pendant tyramide-reactive groups. In another aspect, at least one γPNA residue of the γPNA comprising a pendant tyramide-reactive group is separated from other γPNA residues comprising a pendant tyramide-reactive group by at least one γPNA residue that does not have a tyramide-reactive group. In another aspect, the selectivity component is a gamma peptide nucleic acid (γPNA). In another aspect, the tyramide-reactive moiety is an oligopeptide of up to 25 amino acid residues, comprising a plurality of tyrosine residues, and in another aspect, the tyrosine residues are separated from other tyrosine residues in the tyramide-reactive moiety by at least one different amino acid residue that is not tyrosine, preferably glycine. In a further aspect, the binding reagent is covalently linked to a peroxidase enzyme, such as horseradish peroxidase.

DETAILED DESCRIPTION

Figure 1:
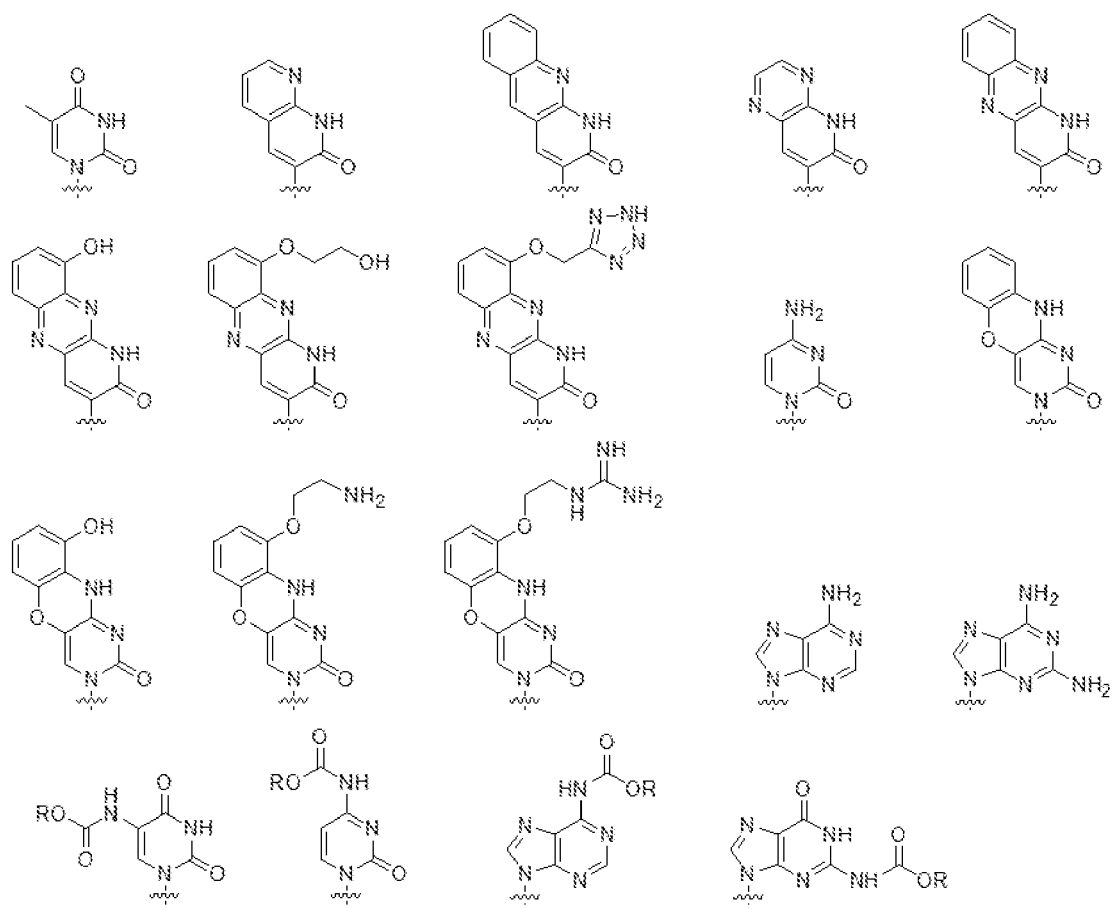
FIG. 1 depicts selected nucleobases.

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

For definitions provided herein, those definitions refer to word forms, cognates and grammatical variants of those words or phrases.

According to one aspect, provided herein are selectivity components, which are binding reagents that bind specifically compounds, molecules or compositions to the substantial exclusion of others in any given assay. Nucleic acids and analogs thereof, collectively "genetic recognition reagents", bind specifically to (hybridize specifically to) a complementary nucleic acid strand under assay conditions by Watson-crick, or Watson-Crick-like base pairing, and typically have 100% or at least 95%, 90%, 80%, 75%, 60%, 50%, and increments therebetween, sequence identity with a complementary target sequence. For selectivity components that do not bind by Watson-Crick base-pairing, but bind by any other mechanism, such as with antibodies, aptamers, ligands, epitopes, etc., the selectivity component binds specifically to a desired target and not to other compounds or compositions in an assay system to any substantial degree. In all instances, the selectivity component is specific enough in its binding to permit specific labeling of a target analyte according to the methods herein with non-interfering cross-reactivity with non-target analytes and/or non-specific binding. Two strands of nucleic acids are considered non-complementary when they do not hybridize under physiological conditions or conditions of a specific assay, and typically contain less than 50% complementarity, meaning that less than 50% of the bases in the two strands are mismatched.

In the context of the present disclosure, a "nucleotide" refers to a monomer comprising a nucleobase and a backbone element, which in a nucleic acid, such as RNA or DNA is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked amines, as are known in the art. A "nucleotide residue" refers to a single nucleotide that is incorporated into an oligonucleotide or polynucleotide. Likewise, a "nucleobase residue" refers to a nucleobase incorporated into a nucleotide or a nucleic acid or analog thereof. A "genetic recognition reagent" refers generically to a nucleic acid or a nucleic acid analog that comprises a sequence of nucleobases that is able to hybridize to a complementary nucleic acid sequence on a nucleic acid by cooperative base pairing, e.g., Watson-Crick base pairing or Watson-Crick-like base pairing.

Nucleobases are recognition moieties that bind specifically to one or more of adenine, guanine, thymine, cytosine, and uracil, e.g., by Watson-Crick or Watson-Crick-like base pairing by hydrogen bonding. A "nucleobase" includes primary nucleobases: adenine, guanine, thymine, cytosine, and uracil, as well as modified purine and pyrimidine bases, such as, without limitation, hypoxanthine, xanthene, 7-methylguanine, 5, 6, dihydrouracil, 5-methylcytosine, and 5-hydroxymethylcytosine. FIG. 1 also depicts non-limiting examples of nucleobases, including monovalent nucleobases (e.g., adenine, cytosine, guanine, thymine or uracil, which bind to one strand of nucleic acid or nucleic acid analogs), and "clamp" nucleobases, such as a "G-clamp," which binds complementary nucleobases with enhanced strength. Additional purine, purine-like, pyrimidine and pyrimidine-like nucleobases are known in the art, for example as disclosed in U.S. Pat. Nos. 8,053,212, 8,389,703, and 8,653,254.

Nucleotides have the structure A-B wherein A is a backbone monomer and B is a divalent nucleobase as described above. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). The backbone monomer includes both the structural "residue" component, such as the ribose in RNA, and any active groups that are modified in linking monomers together (polymerizing), such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl) glycine backbone monomer are condensed during polymerization to leave a peptide (amide) bond. In another embodiment, the active groups are groups useful for phosphoramidite oligomer synthesis, as is broadly-known in the arts. The nucleotide optionally comprises one or more protecting groups as are known in the art, such as 4,4'-dimethoxytrityl (DMT), and as described herein. A number of additional methods of preparing synthetic genetic recognition reagents are known, and depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the particular field of nucleic acid and nucleic acid analog oligomer synthesis.

In certain aspects, nucleic acid selectivity components are nucleic acid analogs, comprising modifications to native nucleic acid structures (RNA and DNA) that increase their stability, including, for example, modifications that provide increased resistance to degradation by enzymes such as endonucleases and exonucleases, and/or modifications that enhance or mediate the utility of the nucleic acid ligand (see, e.g., U.S. Pat. Nos. 5,660,985 and 5,637,459). Examples of such modifications include chemical substitutions at the ribose and/or phosphate and/or base positions, in various aspects, modifications of the nucleic acid ligands may include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanine and the like. Modifications may also include 3' and 5' modifications such as capping. For example, the nucleic acid is an RNA molecule that is 2'-fluoro (2'-F) modified on the sugar moiety of pyrimidine residues.

Figure 2:
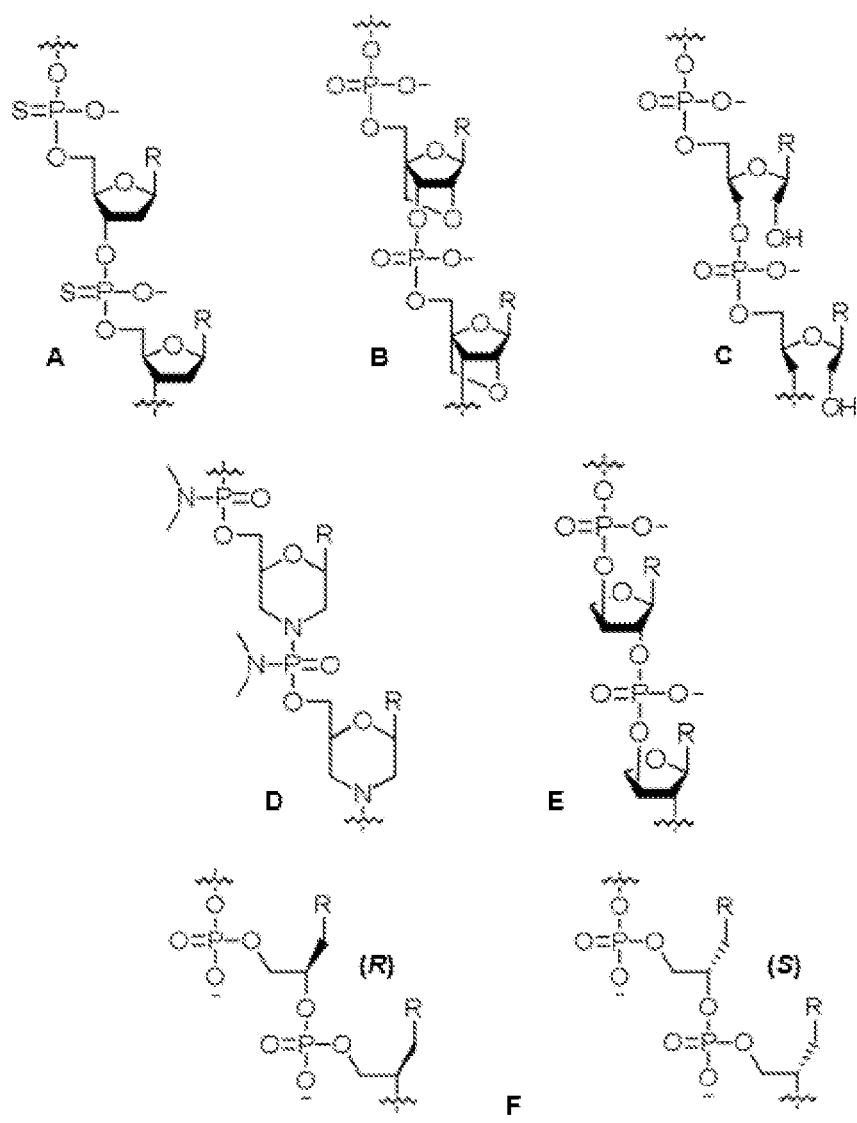
FIG. 2 depicts selected nucleic acid analog backbones.

Non-limiting examples of common nucleic acid analogs include peptide nucleic acids, such as γPNA, phosphorothioate (e.g., FIG. 2A), locked nucleic acid (2'-O-4'-C-methylene bridge, including oxy, thio or amino versions thereof, e.g., FIG. 2B), unlocked nucleic acid (the C2'-C3' bond is cleaved, e.g., FIG. 2C), 2'-O-methyl-substituted RNA, morpholino nucleic acid (e.g., FIG. 2D), threose nucleic acid (e.g., FIG. 2E), glycol nucleic acid (e.g., FIG. 2F, showing R and S Forms), etc. FIG. 2A-2F shows monomer structures for various examples of nucleic acid analogs. FIGS. 2A-2F each show two monomer residues incorporated into a longer chain as indicated by the wavy lines.

Incorporated nucleotide and nucleotide analog monomers are referred to herein as "residues" and the part of the nucleic acid or nucleic acid analog oligomer or polymer excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and thus the backbone monomer is ribose triphosphate prior to incorporation and a ribose monophosphate residue after incorporation.

According to one embodiment, with the advent of conformationally-preorganized γPNA, precise sequence selection is no longer an issue (Bahal, R., et al. "Sequence-unrestricted, Watson-Crick recognition of double helical B-DNA by (R)-MiniPEG-γPNAs (2012) *Chem Bio Chem* 13:56-60). γPNA can be designed to bind to any sequence of double helical B-DNA based on the well-established rules of Watson-Crick base-pairing. Non-limiting examples of γPNA monomers and oligomers are provided below, with, e.g., an amino acid side chain, or a PEGylated (polyethyleneglycol, or PEG) group at the chiral gamma carbon.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer structure. A polymer is said to comprise a specific type of linkage if that linkage is present in the polymer.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). Herein, "nucleic acid" and "oligonucleotide", which is a short, single-stranded structure made up of nucleotides, are used interchangeably. An oligonucleotide may be referred to by the length (i.e. number of nucleotides) of the strand, through the nomenclature "-mer". For example, an oligonucleotide of 22 nucleotides would be referred to as a 22-mer.

A "peptide nucleic acid" refers to a DNA or RNA analog or mimic in which the sugar phosphodiester backbone of the DNA or RNA is replaced by a N-(2-aminoethyl)glycine unit. A gamma PNA (γPNA) is an oligomer or polymer of gamma-modified N-(2-aminoethyl)glycine monomers of the following structure:

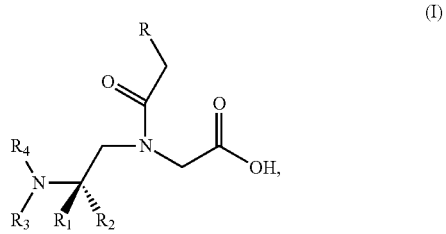

(I)

where at least one of R1 or R2 attached to the gamma carbon is not a hydrogen, or R1 and R2 are different, such that the gamma carbon is a chiral center. When R1 and R2 are hydrogen (N-(2-aminoethyl)-glycine backbone), or the same, there is no such chirality about the gamma carbon. When R1 and R2 are different, such as when one of R1 or R2 are H and the other is not, there is chirality about the gamma carbon. Typically, for γPNAs and γPNA monomers, either of R1 or R2 is an H and the other is an amino acid sidechain or an organic group, such as a ($C_1$-$C_{10}$) organic group or hydrocarbon, optionally PEGylated with from 1 to 50 oxyethylene residues—that is, $[-O-CH_2-CH_2-]_n$, where n is 1 to 50, inclusive. R4 can be H or an organic group, such as a ($C_1$-$C_{10}$) organic group or hydrocarbon, optionally PEGylated with from 1 to 50 oxyethylene residues. For example and without limitation, R1, R2 and R4 are, independently, H, amino acid side chains, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, PEGylated moieties of the preceding comprising from 1 to 50 ($-O-CH_2-CH_2-$) residues, $-CH_2-(OCH_2-CH_2)_qOP_1$, $-CH_2-(OCH_2-CH_2)_q-NHP_1$, $-CH_2-(OCH_2-CH_2-O)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S[CH_2CH_2]_sNHC(NH)NH_2$, where $P_1$ is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)aryl($C_1$-$C_6$)alkylene and ($C_3$-$C_8$)cycloalkyl($C_1$-$C_6$) alkylene; q is an integer from 0 to 10, inclusive; r and s are each independently integers from 1 to 50, inclusive; where R1 and R2 are different, and optionally one of R1 or R2 is H. R3 is H or a protective group, and R is a nucleobase.

The following are exemplary definitions of various moieties or groups as used herein. "Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene ($-CH_2-CH_2-$). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene and propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof. The term "ether" or "oxygen ether" refers to ($C_1$-$C_{10}$)alkyl group wherein one or more of the alkyl group's carbon atoms is replaced with an —O— group. The term ether includes —$CH_2-(OCH_2-CH_2)_qOP_1$ compounds where $P_1$ is a protecting group, —H, or a ($C_1$-$C_{10}$)alkyl. Exemplary ethers include polyethylene glycol, diethylether, methylhexyl ether and the like.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene. As used herein, a "phenol" group is hydroxyphenyl, for example a peptide backbone comprising a hydroxyphenyl group. Tyrosine is an amino acid comprising a 4-hydroxyphenyl group (e.g., L-2-Amino-3-(4-hydroxyphenyl)propanoic acid).

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"$(C_3-C_8)$aryl-$(C_1-C_6)$alkylene" refers to a divalent alkylene wherein one or more hydrogen atoms in the $C_1-C_6$ alkylene group is replaced by a $(C_3-C_8)$aryl group. Examples of $(C_3-C_8)$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene. The term "$(C_3-C_8)$cycloalkyl-$(C_1-C_6)$alkylene" refers to a divalent alkylene wherein one or more hydrogen atoms in the $C_1-C_6$ alkylene group is replaced by a $(C_3-C_8)$cycloalkyl group. Examples of $(C_3-C_8)$cycloalkyl-$(C_1-C_6)$alkylene groups include without limitation 1-cyproylbutylene, cyproyl-2-butylene, cyclopentyl-1-phenyl-2-methylpropylene, cyclobutylmethylene and cyclohexylpropylene.

By "immobilized" in reference to a composition such as a nucleic acid, nucleic acid analog, or polypeptide as described herein, it is meant attached to a substrate of any physical structure or chemical composition. The immobilized composition is immobilized by any method useful in the context of the end use. The composition is immobilized by covalent or non-covalent methods, such as by covalent linkage of amine groups to a linker or spacer, or by non-covalent bonding, including van der Waals and/or hydrogen bonding. In the context of an in situ assay, a target analyte is immobilized in a cell or tissue structure. A "label" is a chemical moiety that is useful in detection of, or purification or a molecule or composition comprising the label. A label may be, for example and without limitation, a radioactive moiety, such as $^{14}C$, $^{32}P$, $^{35}S$, a fluorescent dye, such as fluorescein isothiocyanate or a cyanine dye, an enzyme, or a ligand for binding other compounds such as biotin for binding streptavidin, or an epitope for binding an antibody. A multitude of such labels, and methods of use thereof are known to those of ordinary skill in the immunology and molecular biology arts.

Figure 3A:
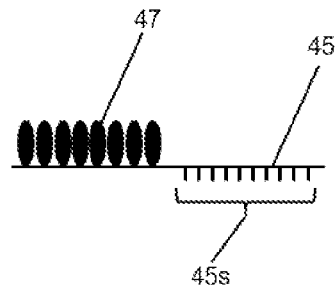
FIGS. 3A-3C depict probe and tyramide-binding tag/moiety arrangements.
Figure 3B:
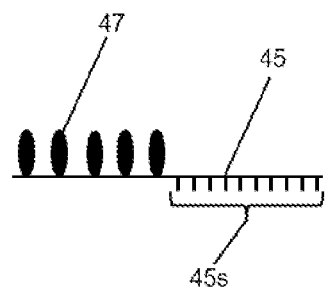
Figure 3C:
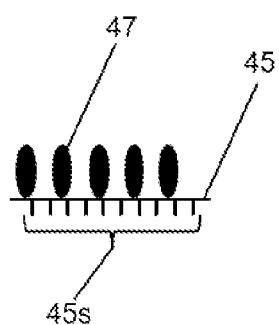

Addition of a tag comprising tyramide-reactive groups to the PNA or γPNA, or to any probe described herein comprising one or more tyramide-reactive groups, can be accomplished in a number of different ways, for instance, as shown schematically in FIG. 3(A-C). In a first aspect depicted in FIG. 3A, probe 45 comprises a separate tyramide-reactive moiety tag comprising tyramide-reactive groups 47. The tyramide-reactive moiety can be any oligomer or polymer comprising tyramide-reactive groups. In one aspect the tyramide-reactive moiety is a polypeptide comprising a plurality of tyrosine residues, such as poly(Tyr) or poly(Tyr, Xaa) where the Tyr residues are combined with one or more residues of one or more additional amino acids, such as Gly. Non-limiting examples of polypeptides comprising Tyr are oligopeptides of from 2 to 20 amino acids in length, including poly(Tyr)$_n$, poly(Tyr-Gly)$_n$, and poly(Tyr-Gly-Gly)$_n$. Other polymers or copolymers, including block-copolymers, and any topology, comprising a plurality of pendant tyramide-reactive groups are contemplated as being suitable as tyramide-reactive moieties, including: polyacrylamides, polyethers (e.g., polyalkylene glycols), polyesters, polyurethanes, etc. The probe 45 comprises a targeting sequence 45S complementary to a target sequence of a target nucleic acid. In a second aspect, shown in FIG. 3B, probe 45 is identical to the probe of FIG. 3A, but the tyramide-reactive groups 47 of the tyramide-reactive moiety are spaced-apart, meaning they are not on adjacent backbone monomers of the tyramide-reactive moiety, for instance when the tyramide-reactive moiety is a PNA. In a third aspect, shown in FIG. 3C, probe 45 does not comprise a separate tyramide-reactive moiety, but the backbone of the probe comprises the tag in the form of a plurality of tyramide-reactive groups within the targeting sequence. For any probe described herein comprising one or more tyramide-reactive groups, the probe may comprise both a tyramide-reactive moiety and the backbone of the probe may comprise one or more tyramide-reactive groups on the backbone of the probe within the targeting sequence.

Figure 4:
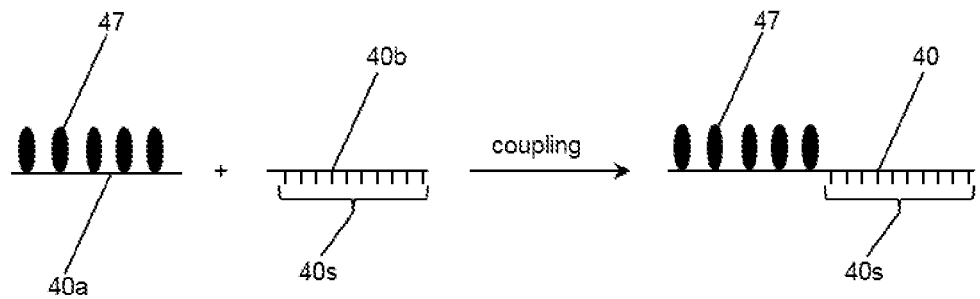
FIG. 4 provides a schematic for making a probe having a tyramide-binding tag/moiety.

FIG. 4 illustrates a method of manufacturing a probe 40 comprising a tag or moiety 40a comprising a plurality of tyramide-reactive groups 47, such as hydroxyphenyl groups, and a selectivity component that is a nucleic acid or nucleic acid analog 40b comprising a sequence of nucleobases 40a specific to a target sequence or for use as an aptamer. Tag 40a is coupled with nucleic acid or nucleic acid analog 40b by any useful coupling chemistry. Methods of coupling using various reactive groups are well-known in the organic chemistry and molecular probes field. Depending on the end structure of tag 40b and nucleic acid or nucleic acid analog 40a, different coupling or linking chemistries and, where necessary chemical linkers can be employed. Typically, tag 40b and nucleic acid or nucleic acid analog 40a are terminated with hydroxyl, carboxyl, phosphate, or amine groups, which are readily joined (See, e.g., Montalbetti, C.A.G.N. et al., "Amide Bond Formation and Peptide Coupling" (2005) *Tetrahedron* 61:10827-10852). Other groups, such as sulfhydryl and isocyanate groups can be used for coupling reactions.

In one aspect, the probe comprising one or more tyramide-reactive groups is a PNA, such as a γPNA. Referring to formula (I), above, for the tyramide-reactive moiety, R can be a tyramide-reactive group, such as hydroxyphenyl or phenylboronic acid. For example, the tyramide-reactive moiety can be an oligomer of from 5 to 25 PNA monomer residues with each instance of R being a tyramide-reactive moiety, or with alternating, or every third, fourth, fifth, etc. PNA monomer residue having a tyramide-reactive group for R, with the rest having for R a group that is non-reactive with the tyramide radical, such as an alkyl group or H. The tyramide-reactive moiety can have the same or different backbone as the sequence-specific portion of the probe. For example, while the sequence-specific portion of the probe may be γPNA, the tyramide-binding moiety can be a polypeptide (e.g. poly(tyrosine) or poly(glycine-tyrosine). As a non-limiting example, the following depicts a structure (II), where n is 1 to 20, including a hydroxyphenyl group for every other R, where R is H, alkyl or any other group that is non-reactive with a tyramide radical. Alternately every instance of R is a tyramide-reactive group, such as hydroxyphenyl or phenylboronic acid.

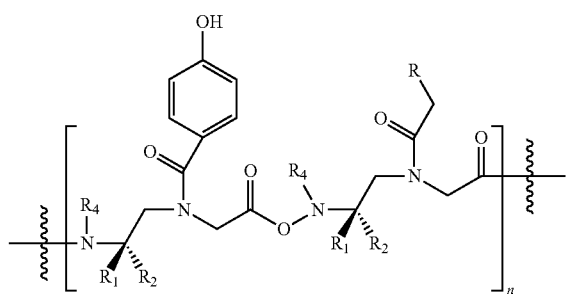

(II)

In another aspect, where the tyramide-reactive groups are incorporated into the backbone of the PNA, e.g., γPNA, within the targeting sequence, in reference to structure (I) and the groups as defined therein, one of R1 or R2 are a tyramide-reactive group, while the other is a different group, such as H. Alternately, or in addition, R4 is a tyramide-reactive group. As a non-limiting example of this is structure (III), where n is 1 to 20, in which R1 is substituted with hydroxyphenyl, with R2 being a different group, in one aspect H, R4 is as defined above, R1 being different from R2, such as a second hydroxyphenyl group, and R is a nucleobase, with the sequence of the nucleobases R forming the targeting sequence.

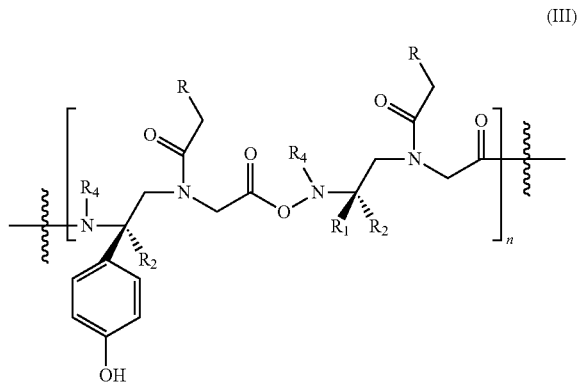

(III)

A γPNA monomer incorporated into a γPNA oligomer or polymer,

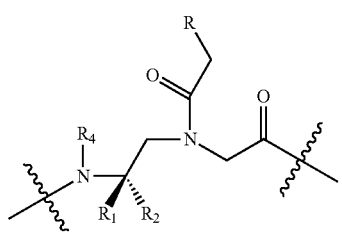

is referred to herein as a "γPNA monomer residue", with each residue having the same or different R group as its nucleobase, such as adenine, guanine, cytosine, thymine and uracil bases, or other nucleobases, such as the monovalent bases described herein, such that the order of nucleobases on the γPNA is its "sequence", as with DNA or RNA. The depicted γPNA monomer and residue structures show a backbone monomer, and a backbone monomer residue, respectively, attached to a nucleobase (R). A sequence of nucleobases in a nucleic acid or a nucleic acid analog oligomer or polymer, such as a γPNA oligomer or polymer, binds to a complementary sequence of adenine, guanine, cytosine, thymine and/or uracil residues in a nucleic acid strand by cooperative bonding, essentially as with Watson-Crick binding of complementary bases in double-stranded DNA or RNA. "Watson-Crick-like" bonding refers to hydrogen bonding of nucleobases other than G, A, T, C or U, such as the bonding of the divalent bases shown herein with G, A, T, C, U or other nucleobases.

Figure 5:
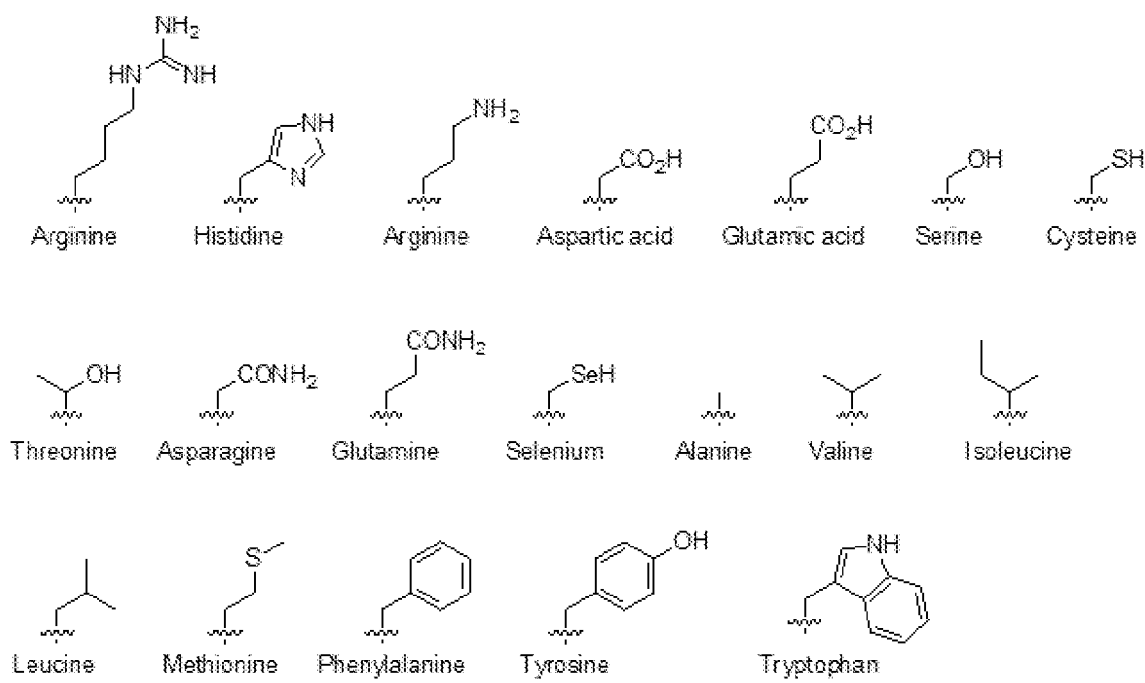
FIG. 5 depicts amino acid side chains.

An "amino acid side chain" is a side chain for an amino acid. Amino acids have the structure:

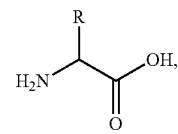

where R is the amino acid side chain. Non-limiting examples of amino acid side chains are shown in FIG. 5. Glycine is not represented because in the embodiment R1s are both H.

Figure 6A:
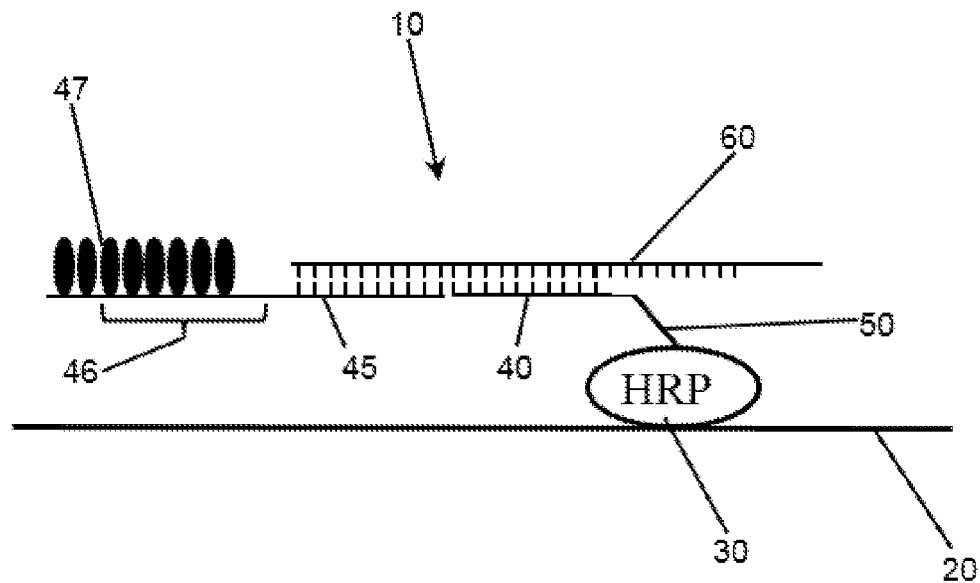
FIGS. 6A and 6B depict schematically complexes formed in aspects of the methods described herein, in which the target analyte is a nucleic acid.

FIG. 6A depicts schematically a first aspect of the invention. In this aspect, a complex 10 is provided. The complex 10 comprises a substrate 20 having a peroxidase 30, such as horseradish peroxidase (HRP), bound to the substrate 20 either covalently, such as by a linker or non-covalently, such as by adsorption or via an antibody or use of binding partners. The substrate 20 can be any useful structure to which the HRP is bound, such as a plate, well, array, chip, particle, bead, etc. Peroxidase 30 is attached to a first probe 40 via a linking structure 50, which can be a covalent linker (linking group), as are broadly known in the art, or can be linked non-covalently, for example by use of binding partners, such as streptavidin/biotin, as described below. The linking structure 50 can be any moiety or combination of moieties so long as they do not interfere with the peroxidase activity of the peroxidase 30, and the ability of the first probe 40 to bind specifically to (hybridize to) a first target site of a target sequence 60 by Watson-Crick or Watson-Crick-like hydrogen bonding. Useful linking groups for the linking structure 50 are broadly-known and can be determined without undue experimentation. Second probe 45 is shown, including a nucleobase sequence complementary to a second target site of the target sequence 60, different from the first target site. The second probe 45 includes a plurality of tyramide-binding groups 47. In one aspect, the plurality of tyramide-binding groups 47 are one or more hydroxyphenyl groups, e.g., 4-hydroxy-phenyl groups and/or one or more phenylboronic acid groups, such as a 4-phenylboronic acid group. Of note, 5' to 3' directionality of the target sequence is immaterial, so long as the first probe 40 and second probe 45 bind specifically to the target sequence. Likewise, the location of, and order of the first and second target site on the target sequence 60 are immaterial, so long as the tyramide-binding groups 47 are able to bind free tyramide radicals in solution. In use, the presence of the target sequence 60 results in co-localization of the peroxidase 30 and the tyramide-binding groups 47, such that when a labeled tyramide compound is added to the reaction, tyramide radicals are formed, and the labeled tyramide compound deposits at the tyramide-binding groups 47. Additional probes having the structure of second probe 45, but with a different target site on the target sequence 60 than the first and second target sites may be employed, providing additional tyramide-binding groups. In the absence of the target sequence 60, the second probe 45 is washed away prior to addition of the labeled tyramide compound, and does not co-localize with the peroxidase 30, such that tyramide radicals of the labeled tyramide compound are not deposited or co-localized, but dimerize and can be washed away.

Figure 6B:
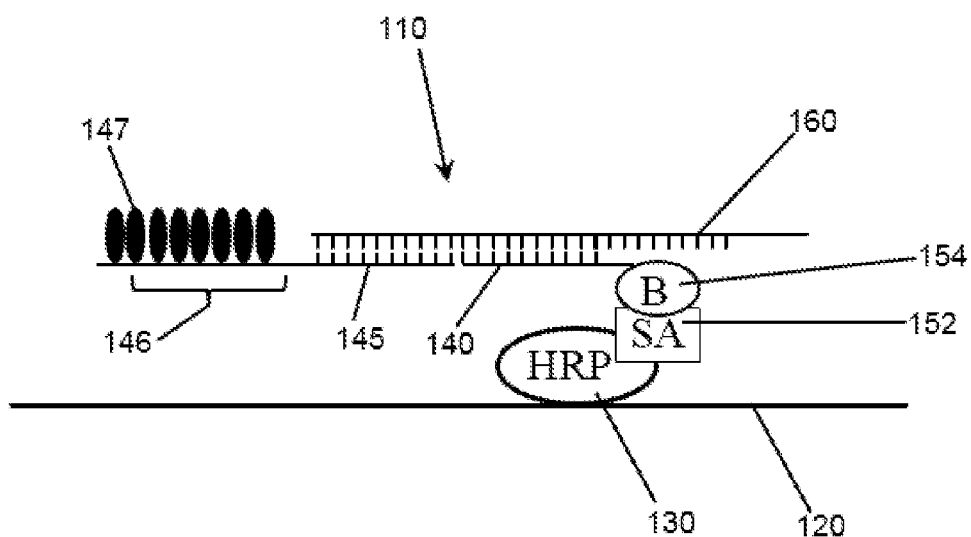

FIG. 6B depicts a further aspect of the invention. As in FIG. 6A, the complex 110 includes a substrate 120, a peroxidase, a first probe 154, a second probe 145 labeled with tyramide-reactive groups 147, and a target sequence. Linking structure depicted in FIG. 6A is a streptavidin 152 and biotin 154 binding pair. Streptavidin 152 is linked, covalently or non-covalently, with peroxidase 130, while biotin 154 is linked, typically covalently, to biotin 154. The benefit to this structure is that a substrate 110 comprising the linked streptavidin 152 and peroxidase 130 pair can be prepared, such as a multi-well or array substrate, and different first and second probes can be used on the same plate, and even in the same well or array location to test for the presence of different target sequences in a sample.

The structure depicted in FIG. 6A might be preferable in many instances, such as on a manufactured array chip, with many very small discrete locations, such that combinations of peroxidase 30, linking structure, preferably a covalent linker, and first probe 40 will remain at a discrete location under most product distribution, storage, and assay conditions. An array chip may be preferable where a single sample, such as a whole-cell RNA sample, is being tested for a large number of different sequences. To the contrary, the structure depicted in FIG. 6B might be preferable where the assay is conducted in a multi-well plate, allowing flexibility of which probe set to use in any given circumstance.

Figure 7A:
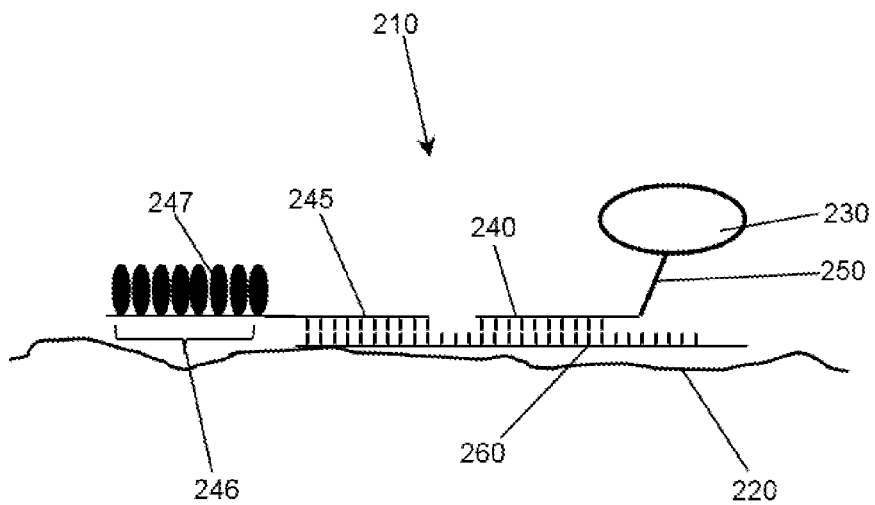
FIGS. 7A and 7B depict schematically complexes formed in aspects of the in situ methods described herein, in which the target analyte is a nucleic acid.
Figure 7B:
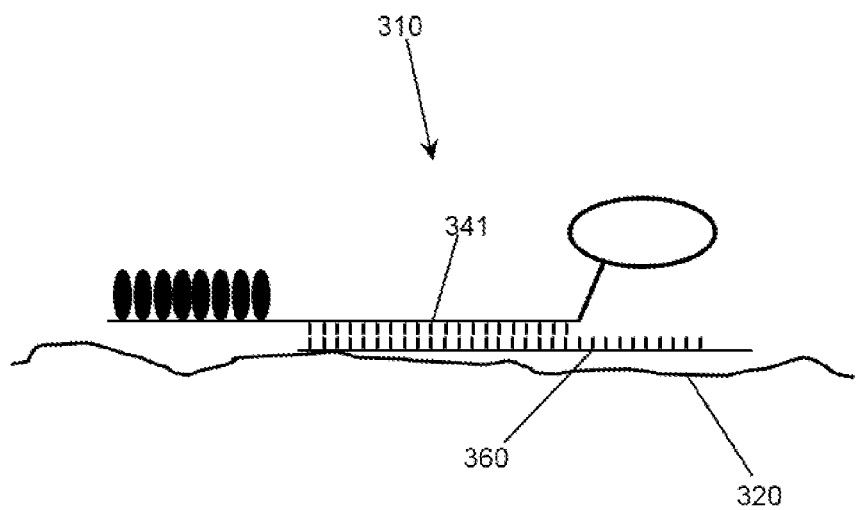

FIGS. 7A and 7B depict alternative aspects of a complex 210 and 310, respectively for detection of nucleic acids in situ. The complexes 210 and 310 of FIGS. 7A and 7B are identical except for the probe design. In FIGS. 7A and 7B, the substrate 220 and 320 is cell or tissue material comprising a target sequence 260 and 360, such as a DNA or RNA, such as a microRNA. The cell or tissue material is typically affixed to a suitable surface, such as a microscope slide according to any useful methodology. FIG. 7A depicts a two mini-probe design with first probe 240 hybridized to a complementary target within target sequence 260. The first probe 240, is referred to herein as a selectivity component, and is conjugated to a peroxidase 230 by linking structure 250 that can be a direct covalent link via a linker, or a binding pair, where, for example, probe 240 is biotinylated and the peroxidase 230 is conjugated with streptavidin. The peroxidase is co-localized with the tyramide-binding groups by hybridization of a second probe 245 having a tyramide-binding moiety 246 comprising tyramide-binding groups 247, such as hydroxyphenyl groups, attached thereto. As above, contacting labeled tyramide compounds with the peroxidase results in conjugation of the labeled tyramide compounds with the tyramide-binding groups 247. FIG. 7B depicts a single probe 341 attached to both the tyramide-binding moiety and the peroxidase. As indicated herein, the two-probe (two selectivity component) system of FIG. 7A may be preferable to the single-probe approach of FIG. 7B.

Figure 8A:
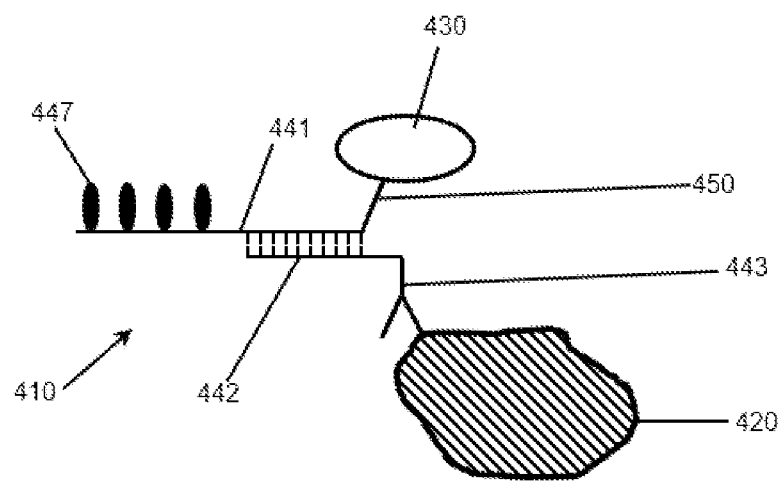
FIGS. 8A-8C depict schematically complexes formed in aspects of the methods described herein, in which the target analyte is a protein.
Figure 8B:
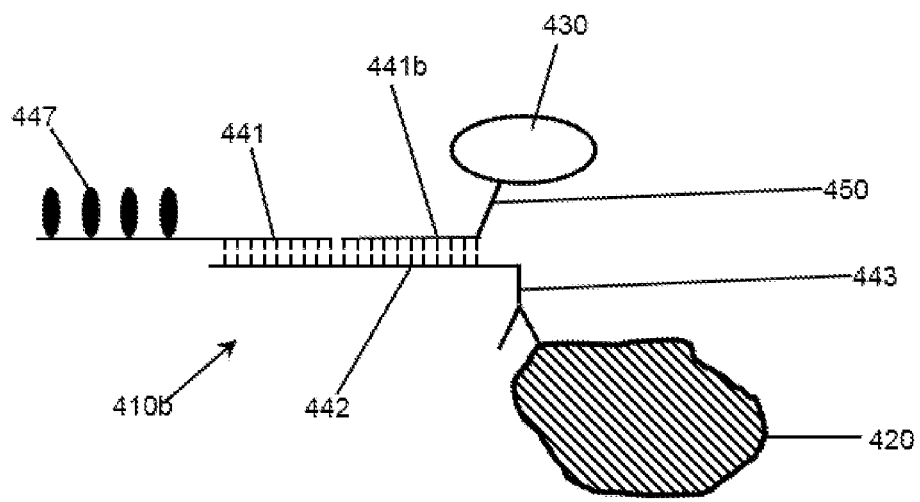
Figure 8C:
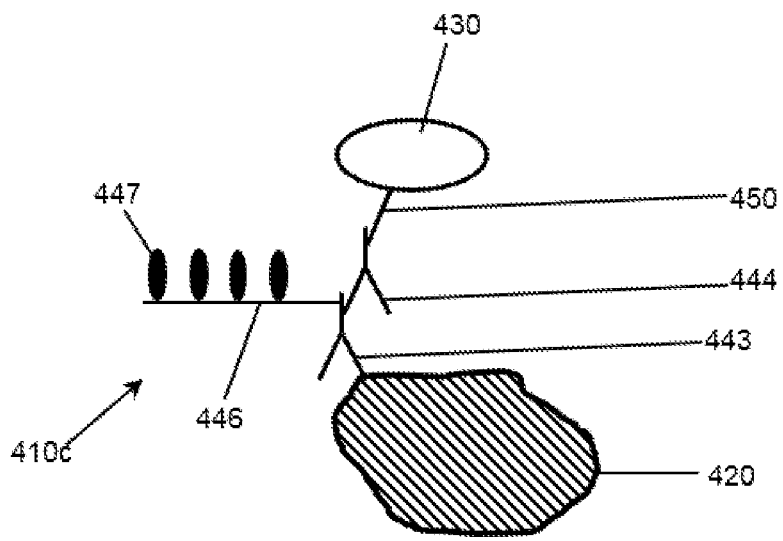

FIGS. 8A, 8B and 8C depict alternate aspects of a complex 410, 410b, and 410c, respectively, where an antibody selectivity component binds a target protein. As with the nucleic acid of FIGS. 6A, 6B, 7A and 7B, the target protein can be detected in situ or the assay may be performed on a plate or other substrate. FIGS. 8A, 8B, and 8C show aspects of an in situ detection method with protein 420 being affixed within cellular or tissue material. In FIGS. 8A, 8B, and 8C, protein is bound to an antibody 443 as the selectivity component. Tyramide-binding moiety 446, comprising a plurality of spaced-apart tyramide-binding groups 447, such as hydroxyphenyl groups, are depicted, as well as a peroxidase 430 and a linking structure 450 as described above, such as a biotin/streptavidin pair or a linker. In FIGS. 8A and 8B, the antibody 443 is conjugated to a target sequence 442, which is used, in turn to complex the peroxidase 230 and tyramide-binding moiety 446 in a single-probe 441 configuration as shown in FIG. 8A, or a two-probe 441 and 441b configuration as shown in FIG. 8B. FIG. 8C shows the tyramide-binding moiety 446 conjugated to the antibody 443, and the peroxide 430 attached via linking structure 450 to a secondary antibody 444 that binds the antibody 443. As above, addition of labeled tyramide results in the binding of the labeled tyramide to tyramide-binding groups 447.

Figure 9:
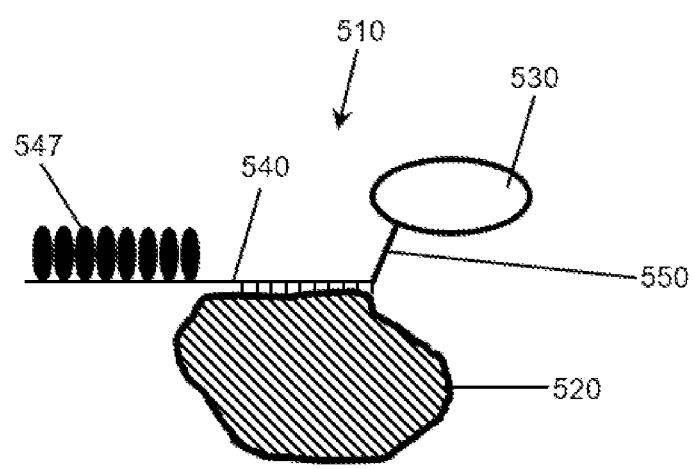
FIG. 9 depicts schematically a complex formed in an aspect of the methods described herein, in which the target analyte is a nucleic acid and the selectivity component is an aptamer.

FIG. 9 depicts an aspect in which the selectivity component is a nucleic acid ligand or aptamer. Complex 510 comprises protein 520, and an aptamer 540 linked to a tyramide-binding moiety comprising tyramide-binding groups 547, and a peroxidase 530 attached to the aptamer by a linking structure, which may be a direct linker or a binding pair, such as biotin-streptavidin. As before, labeled tyramide is activated by the peroxidase 530 and binds tyramide-binding groups 547.

FIGS. 6A, 6B, 7A, 7B, 8A, 8B, 8C, and 9 show various complexes embodying various methods of co-localizing, through use of a selectivity component that selectively binds a target analyte, the target analyte, such as a protein or nucleic acid, a peroxidase, and a plurality of tyramide-binding groups. Based on this disclosure, the choice of various binding reagents, linkers, selectivity components, peroxidases, tyramide labels, and tyramide-binding groups would be a matter of design choice. As a non-limiting example, the tyramide-binding moiety may be a biotin-streptavidin complex, with streptavidin being linked to the selectivity component, and biotinylated polytyrosine or biotinylated tyramide-binding moieties being bound to the streptavidin, providing up to a four-fold multiplication of tyramide-binding groups in the complex.

In certain aspects, the selectivity component is an antibody or an antibody fragment. For example, activators may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

In one aspect, the selectivity component is an antibody. Preparation of antibodies may be accomplished by any number of well-known methods for generating monoclonal antibodies. These methods typically include the step of immunization of animals, typically mice; with a desired immunogen (e.g., a desired target molecule-or fragment thereof). Once the mice have been immunized, and preferably boosted one or more times with the desired immunogen(s), monoclonal antibody-producing hybridomas may be prepared and screened according to well-known methods (see, for example, Owen, J. A. et al., KUBY IMMUNOLOGY, Seventh Edition, pp. 654-656, W.H. Freeman & Co. (2013), for a general overview of monoclonal antibody production). Production of antibodies and other binding reagents have become extremely robust. In vitro methods that combine antibody recognition and phage display techniques allow one to amplify and select antibodies or other binding reagents with very specific binding capabilities. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In another aspect, the selectivity component is an antibody fragment. Selection and preparation of antibody fragments may be accomplished by any number of well-known methods. Phage display, bacterial display, yeast display, mRNA display and ribosomal display methodologies may be utilized to identify and clone desired antibody fragment activators that are specific for a desired target molecule, including, for example, Fab fragments, Fvs with an engineered intermolecular disulfide bond to stabilize the $V_H$-$V_L$ pair, scFvs, or diabody fragments. Production of scFv antibody fragments using display methods, including phage, bacterial, yeast, ribosomal and mRNA display methods can be employed to produce the activator and/or selectivity component, as described herein. As described below, yeast display methods were used to produce an activator described below. Yeast display methods are described, for example, in Boder, et al. (2000) Proc. Natl. Acad. Sci USA 97:10701-5; Swers, et al. (2004) Nucl. Acids. Res. 32: e36; and Yeast Display scFv Antibody Library User's Manual, Pacific Northwest National Laboratory, Richland, Wash. 99352, Revision Date: MF031112.

Ribosome display also is a useful method for producing the activator and/or the selectivity component. Ribosome display is a technique used to perform in vitro protein evolution to create proteins that can bind to a desired ligand. The process results in translated proteins that are associated with their mRNA progenitor which is used, as a complex, to bind to an immobilized ligand in a selection step. The mRNA encodes random polypeptides, and the diversity can far exceed that of phage and yeast display systems. The mRNA-protein hybrids that bind well to a ligand are then reverse transcribed to cDNA and their sequence amplified via PCR. The end result is a nucleotide sequence that can be used to create tightly binding proteins. (see, e.g., Hanes J, et al., (1997) *Proc Natl Acad Sci USA* 91:4937-4942; He M, Taussig M J (1997) Nucleic Acids Res 25:5132-5134; and In Vitro Protein Expression Guide, PROMEGA (2005), pp-29-33, Chapter 6, Ribosome Display))

Ribosome display either begins with a DNA sequence or naive library of sequences coding for a specific protein. The sequence is transcribed, and then translated in vitro into protein. However, the DNA library coding for a particular library of binding proteins is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. What results is a complex of mRNA, ribosome, and protein which can bind to surface-bound ligand. This complex is stabilized with the lowering of temperature and the addition of cations such as $Mg^{2+}$.

During the subsequent binding, or panning, stages, the ribosome complex is introduced to surface-bound ligand. This can be accomplished several ways, for example using an affinity chromatography column with a resin bed containing ligand, a 96-well plate with immobilized surface-bound ligand, or magnetic beads that have been coated with ligand. The complexes that bind well are immobilized. Subsequent elution of the binders via high salt concentrations, chelating agents, or mobile ligands which complex with the binding motif of the protein allow dissociation of the mRNA. The mRNA can then be reverse transcribed back into cDNA, undergo mutagenesis, and iteratively fed into the process with greater selective pressure to isolate even better binders.

As it is performed entirely in vitro, there are two main advantages of ribosomal display methods over other selection technologies. First, the diversity of the library is not limited by the transformation efficiency of bacterial cells, but only by the number of ribosomes and different mRNA molecules present in the test tube. Second, random mutations can be introduced easily after each selection round, as no library must be transformed after any diversification step. This allows facile directed evolution of binding proteins over several generations.

In certain display methods, such as phage and yeast display, a library of $V_H$ and $V_L$ chains are prepared from mRNA of B-cells from either naive or immunized animals (such as a mouse, rabbit, goat or other animal), or even from polyclonal or monoclonal hybridoma. The mRNA is reverse-transcribed by known methods using either a polyA primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In display vectors, the $V_H$-linker-$V_L$ sequence is cloned into a surface protein (e.g., for M13, the surface proteins g3p (pHI) or g8p, most typically g3p). Display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from GE Healthcare, Piscataway, N.J. Phage display systems, their construction and screening methods are described in detail in, among others, U.S. Pat. Nos.

5,702,892, 5,750,373, 5,821,047 and 6,127,132, each of which are incorporated herein by reference in their entirety.

Typically, once a population of clones, such as phage, yeast, bacteria, ribosomes, etc., are produced that display a desired polypeptide, such as an antibody fragment, epitope specific clones are selected by their affinity for the desired immunogen. Typically the immunogen is fixed to a surface and the clones are contacted with the surface. Non-binding clones are washed away while binding clones remain bound. Bound clones are eluted and propagated to amplify the selected clones. A number of iterative rounds of affinity selection typically are used, often increasingly higher stringency washes, to amplify immunogen binding clones of increasing affinity. Negative selection techniques also may be used to select for lack of binding to a desired target. In that case, un-bound (washed) clones are amplified. High throughput methods, such as flow cytometry methods, may initially be employed to select clones, followed, optionally by detection of fluorescence in plated colonies by fluorescent imaging techniques.

Although it is preferred to use spleen cells and/or B-lymphocytes from animals preimmunized with a desired immunogen as a source of cDNA from which the sequences of the $V_H$ and $V_L$ chains are amplified by RT-PCR, naive (un-immunized with the target immunogen) splenocytes and/or B-cells may be used as a source of cDNA to produce a polyclonal set of $V_H$ and $V_L$ chains that are selected in vitro by affinity, typically by the above-described phage display (phagemid) method. When naive B-cells are used, during affinity selection, the washing of the first selection step typically is of very high stringency so as to avoid loss of any single clone that may be present in very low copy number in the polyclonal phage library. By this naive method, B-cells may be obtained from any polyclonal source, B-cell or splenocyte cDNA libraries also are a source of cDNA from which the $V_H$ and $V_L$ chains may be amplified. For example, suitable murine and human B-cell, lymphocyte and splenocyte cDNA libraries are commercially available from Agilent Technologies and from Thermofisher—Invitrogen. Phagemid antibody libraries and related screening services are provided commercially by MorphoSys AG, of Martinsried/Planegg, Germany (CysDisplay™).

The selectivity component does not have to originate from biological sources, such as from naive or immunized immune cells of animals or humans. The activator and/or the selectivity component may be screened from a combinatorial library of synthetic peptides. One such method is described in U.S. Pat. No. 5,948,635, incorporated herein by reference, which described the production of phagemid libraries having random amino acid insertions in the pill gene of M13. These phage may be clonally amplified by affinity selection as described above.

Panning in a culture dish or flask is one way to physically separate binding clones from non-binding clones. Panning may be carried out in 96 well plates in which desired immunogen structures have been immobilized. Functionalized 96 well plates, typically used as ELISA plates, may be purchased from Thermo Scientific of Waltham, Massachusetts. Other affinity methods for isolating clones having a desired specificity include affixing a target peptide to beads. The beads may be placed in a column and clones may be bound to the column, washed and eluted according to standard procedures. Alternatively, the beads may be magnetic so as to permit magnetic separation of the binding particles from the non-binding particles. The target peptide also may be affixed to a porous membrane or matrix, permitting easy washing and elution of the binding clones.

In certain aspects, it may be desirable to increase the specificity of the activator for a given target molecule or reporter molecule using a negative selection step in the affinity selection process. For example, activator-displaying clones may be contacted with a surface functionalized with peptides (e.g., proteins, oligopeptides, etc.) distinct from the target molecule or reporter molecule. Clones are washed from the surface and non-binding clones are grown to clonally expand the population of non-binding clones thereby deselecting clones that are not specific for the desired target molecule. In certain embodiments, random synthetic peptides may be used in the negative selection step. In other embodiments, one or more immunogens having structural similarity to the target peptide may be used in the negative selection step. Screening of activators will best be accomplished by high throughput parallel selection, as described in Holt, L. J., et al. (*Current Opinion in Biotechnology* (2000) 11:445-449). Alternatively, high throughput parallel selection may be conducted by commercial entities, such as by MorphoSys AG.

In certain aspects, it may be desirable to mutate the binding region of the selectivity component and select for selectivity components with superior binding characteristics as compared to an un-mutated selectivity component. This may be accomplished by any standard mutagenesis technique, such as by PCR with Taq polymerase under conditions that cause errors. In such a case, the PCR:primers could be used to amplify scFv- or binding reagent-encoding sequences of (e.g.) phagemid plasmids under conditions that would cause mutations. The PCR product may then be cloned into (e.g.) a phagemid vector and screened for the desired specificity, as described above.

Other forms of mutagenesis may be utilized to generate a combinatorial library. For example, mutants may be generated and isolated from a library by screening using, for example, alanine scanning mutagenesis and the like, by linker scanning mutagenesis; by saturation mutagenesis; by PCR mutagenesis; or by random mutagenesis. Linker scanning mutagenesis, particularly in a combinatorial setting, is an attractive method for identifying selectivity components.

In other aspects, the selectivity components are modified to make them more resistant to cleavage by proteases. For example, the stability of the selectivity components that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the activators may be of the D configuration. The switch from L to D amino acids neutralizes the digestion capabilities of many of the ubiquitous peptidases found in the digestive tract. Alternatively, enhanced stability of the activators of the invention may be achieved by the introduction of modifications of the traditional peptide linkages. For example, the-introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the activators may be achieved by intercalating one or more dextrorotatory amino acids (such as, dextrorotatory phenylalanine or dextrorotatory tryptophan) between the amino acids of the activator, in exemplary embodiments, such modifications increase the protease resistance of the selectivity component without affecting their activity or specificity of interaction with a desired target molecule or reporter molecule. Affinity screening, as described above, may be conducted with such modified polypeptides so as to ensure optimal affinity.

In still other aspects, the selectivity component may be an aptamer, also known as a nucleic acid ligand. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired target peptide is bound, followed by polymerase chain reaction (PCR) to amplify nucleic acids that bind to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof as described herein, such as, without limitation, peptide nucleic acids, including γPNA, and phosphorothioate nucleic acids. Aptamers, may be prepared using the "SELEX" methodology which involves selection of nucleic acid ligands which interact with a target in a desirable manner combined with amplification of those selected nucleic acids. The SELEX process, is described in U.S. Pat. Nos. 5,475,096 and 5,270,163 and PCT Application No. WO 91/19813. In certain aspects, nucleic acid ligand selectivity components as described herein are nucleic acid analogs, as described above.

The SELEX process provides a class of products which are nucleic acid molecules, each having a unique sequence, and each of which has the property of binding specifically to a desired target compound or molecule. In various embodiments, target molecules may be, for example, proteins, carbohydrates, peptidoglycans or small molecules. SELEX methodology can also be used to target biological structures, such as cell surfaces or viruses, through specific interaction with a molecule that is an integral part of that biological structure. The basic SELEX method has been modified to achieve a number of specific objectives. For example, U.S. Pat. No. 5,707,796 describes the use of the SELEX process in conjunction with gel electrophoresis to select nucleic acid molecules with specific structural characteristics, such as bent DNA. U.S. Pat. No. 5,580,737 describes a method for identifying highly specific nucleic acid ligands able to discriminate between closely related molecules, termed CounterSELEX. U.S. Pat. No. 5,567,588 describes a SELEX-based method which achieves highly efficient partitioning between oligonucleotides having high and low affinity for a target molecule. U.S. Pat. Nos. 5,496,938 and 5,683,867 describe methods for obtaining improved nucleic acid ligands after SELEX has been performed.

In certain aspects, a selectivity component may contain a tag or handle which facilitates its isolation, immobilization, identification, or detection and/or which increases its solubility. In various embodiments, the tag may be a polypeptide, a polynucleotide, a carbohydrate, a polymer, or a chemical moiety and combinations or variants thereof. In certain embodiments, exemplary chemical handles, include, for example, glutathione S-transferase (GST), protein A, protein G, calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc. In the example of probes described herein, the tyramide-reactive moiety is a tag that comprises a tyramide-reactive group.

In another aspect, a selectivity component is modified so that its rate of traversing the cellular membrane is increased. For example, the selectivity component may be attached to a peptide which promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the *Drosophila* Antennapedia protein, or homologs thereof. The 60 amino acid long homeodomain of the homeo-protein antennapedia has been demonstrated to translocate through biological membranes and can facilitate the translocation of heterologous polypeptides to which it is coupled. Thus, selectivity components may be fused to a peptide consisting of about amino acids 42-58 of *Drosophila* Antennapedia, or shorter fragments, for transcytosis (Derossi et al. (1996) and *J Biol Chem* 271:18188-18193). The transcytosis polypeptide may also be a non-naturally-occurring membrane-translocating sequence (MTS), such as the peptide sequences disclosed in U.S. Pat. No. 6,248,558.

In another aspect, the selectivity component is a nucleic acid or nucleic acid analog, such as PNA, for example γPNA as described above. As depicted in FIGS. 6A and 7A, where the selectivity component is a nucleic acid or nucleic acid analog, the selectivity component can have a split-probe design, as opposed to the unitary probe design of FIGS. 6B and 7B. In the case of a protein, a dual-probe design can be employed where, for example, two antibodies to different epitopes of a target protein, such that both antibodies can simultaneously bind the protein, can be employed, where one protein is conjugated to the tyramide-binding moiety and the other is bound to or attached to a peroxidase.

Unless otherwise indicated, the nucleic acids and nucleic acid analogs described herein are not described with respect to any particular sequence of bases. The present disclosure refers to selectivity components, such as polypeptides (peptides) and nucleic acids and analogs thereof for use in a tyramide-based signal amplification method and system. The usefulness of any specific embodiments utilizing a nucleic acid or nucleic acid analog as a selectivity component, while depending upon a specific sequence in each instance, is generically applicable. Based on the abundance of published work with nucleic acids, nucleic acid analogs and PNA (e.g., γPNA), it is expected that any nucleobase sequence attached to the backbone of the described γPNA oligomers would hybridize in an expected, specific manner with a complementary nucleobase sequence of a target nucleic acid or nucleic acid analog by Watson-Crick or Watson-Crick-like hydrogen bonding. One of ordinary skill would understand that the compositions and methods described herein are sequence-independent and describe novel, generalized compositions.

A "selectivity component" is a molecular recognition unit, such as a polypeptide, polypeptide analog, glycoprotein, nucleic acid, nucleic acid analog, polysaccharide, ligand, or any other molecule or composition that recognizes and binds specifically to a target analyte, e.g., a biomolecule, such as an RNA, DNA, protein, glycoprotein, polysaccharide, lipid, or other cellular constituent, or combinations thereof with limited or no cross-reactivity to other compounds or compositions in a given assay system, such as in an in situ assay, an array, etc. In one aspect, the selectivity component is a γPNA. In another, it is an antibody.

In one aspect, the selectivity component is a nucleic acid or an analog thereof. The nucleic acid or an analog thereof can be a nucleic acid ligand (aptamer) or a genetic recognition reagent. A genetic recognition reagent, hybridizes to a complementary nucleic acid or nucleic acid analog sequence under applicable hybridization conditions for a given assay by Watson-Crick or Watson-Crick-like base pairing. The genetic recognition reagent comprises a backbone and nucleobases. This structure is shown schematically in Formula (IV):

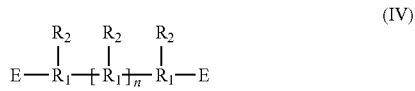

(IV)

where R1 is a backbone monomer residue and R2s are, independently nucleobases, E are independently end (terminal) groups that are part of the terminal monomer residues, and "n" is any positive integer or 0, for example 48 or less, 28 or less, 23 or less, and 18 or less, including 0, 1, 2, 3, 4, 5, 6, 7, 8, 9, 10, 11, 12, 13, 14, 15, 16, 17, and 18. Typically, all instances of R1 are the same with the exception of the terminal monomer residues which typically have different end-groups E as compared to internal monomers, such as, without limitation —$NH_2$ and —C(O)OH or —$CONH_2$ at the respective N-terminal and C-terminal ends for PNAs, and hydroxyl groups at the 5' and 3' ends of nucleic acids.

In one aspect, the selectivity components are implemented on an array. Arrays are particularly useful in implementing high-throughput assays, such as genetic detection assays. As used herein, the term "array" refers to reagents, for example the probes described herein, located at two or more discrete, identifiable and/or addressable locations on a substrate. In one embodiment, an array is an apparatus having two or more discrete, identifiable reaction chambers, such as, without limitation a 96-well dish, in which reactions comprising identified constituents are performed. In an exemplary aspect, selectivity components, such as nucleic acid or nucleic acid analog genetic recognition reagents, for binding one or more target analytes, are immobilized onto a substrate in a spatially addressable manner so that selectivity components are located at two or more different and (addressable) identifiable locations on the substrate. Substrates include, without limitation, multi-well plates, silicon chips and beads. For substrates with two or more addressable locations on a single substrate, such as a chip or multi-well plate, the same and/or different selectivity components can be placed at discrete locations on the substrate. In one embodiment, the array comprises two or more sets of beads, with each bead set having an identifiable marker, such as a quantum dot or fluorescent tag, so that the beads are individually identifiable using, for example and without limitation, a flow cytometer. Each set of the two or more sets of beads comprises a different selectivity component, permitting identification of at least two different target analytes in a single reaction. In each instance, at any single, discrete location on an array, more than one selectivity component may be employed, thereby multiplexing the assay. Where an assay is multiplexed, binding of different target analytes to different selectivity components are independently identifiable, such as by producing a different detection signal such as by producing different colors, or, for fluorochromes, having different excitation and or emission wavelengths and/or intensities. Binding events for each different selectivity component in multiplexed reactions can be detected at the same time or at a different time, for example by producing different emission wavelengths using the same excitation spectrum, or by measuring spectra at different time points. In one embodiment, an array is a multi-well plate containing two or more wells with the described selectivity components for binding specific target analytes. As such, reagents, such as probes and primers may be bound or otherwise deposited onto or into specific locations on an array. Reagents may be in any suitable form, including, without limitation: in solution, dried, lyophilized or glassified. When linked covalently to a substrate, such as an agarose bead or silicon chip, a variety of linking technologies are known for attaching chemical moieties, such as the genetic recognition reagents to such substrates. Linkers and spacers for use in linking nucleic acids, peptide nucleic acids and other nucleic acid analogs are broadly known in the chemical and array arts and for that reason are not described herein. As a non-limiting example, a γPNA genetic recognition reagent contains a reactive amine, which can be reacted with carboxyl, cyanogen bromide-, N-hydroxysuccinimide ester-, carbonyldiimidazole- or aldehyde-functional agarose beads, available, for instance from Thermo Fisher Scientific (Pierce Protein Biology Products), Rockford, Illinois and a variety of other sources. The genetic recognition reagents described herein can be attached to a substrate in any manner, with or without linkers. Informatics and/or statistical software or other computer-implemented processes for analyzing array data and/or identifying genetic risk factors from data obtained from a patient sample, are known in the art.

Thus, according to one embodiment of the present invention, a method is provided for detection of a target sequence in a nucleic acid, comprising contacting a genetic recognition reagent as described herein with a sample comprising nucleic acid and detecting binding of the genetic recognition reagent with a nucleic acid in any manner described herein. In one embodiment, the genetic recognition reagent is immobilized on a substrate, e.g., as depicted in FIGS. 6A and 6B, for example in an array, and the assay is carried out as described, such that the described target sequence 60 and 160, if present binds the immobilized selectivity component, first probes 40 and 140, and second probes 45 and 145 are contacted with the immobilized target sequence 60 and 160, and a labeled tyramide reagent is contacted with the complex such that a labeled tyramide radical is formed, which, in turn binds to the tyramide-reactive groups 47 and 147. Detection of the bound labeled tyramide is accomplished by any useful method by which the label of the bound labeled tyramide can be detected.

TSA is an enzyme-mediated detection method that utilizes the catalytic activity of a peroxidase, such as horseradish peroxidase (HRP), to generate high density labeling of a target protein or nucleic acid sequence in situ. TSA labeling is a combination of three elementary processes. The first step is the binding of a probe to the target via affinity (proteins, aptamers, etc.) or hybridization (nucleic acids) followed by secondary detection of the probe with an HRP-labeled antibody or, as in one aspect of the present invention, a streptavidin conjugate. The second step is activation of multiple copies of a labeled tyramide derivative (e.g., dye- or ligand-/hapten-labeled) by HRP. One example of a labeled tyramide is tyramide with an Alexa 488 label. Finally, covalent coupling of the resulting highly reactive, short-lived tyramide radicals to nucleophilic residues in the vicinity of the HRP-target interaction site occurs, resulting in minimal diffusion-related loss of signal localization.

In one aspect, the labeled tyramide has the structure:

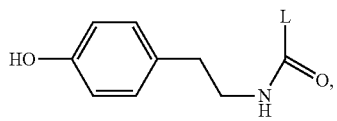

in which L is a detectable moiety, such as a dye, a fluorescent dye, a hapten, a ligand, an enzyme, an epitope, etc. In one aspect, L is a fluorescent dye. A complete list of fluorescent dyes is beyond this disclosure, but a large number of dyes capable of conjugation to the tyramide structure are broadly and commercially available, and methods of conjugating the label moiety L to the tyramide structure are broadly-known. Common fluorescent dyes include fluorone dyes (e.g., fluorescein dyes such as fluorescein isothiocyanate (FITC) and rhodamine dyes), cyanine (e.g., polymethine dyes, such as Cy3 dyes, Cy5 dyes), Alexa Fluor dyes, etc.

In addition to single-labels, members of FRET (Fluorescence/Forster Resonance Energy Transfer) pairs can be attached to different tyramide moieties or to the same tyramide moiety, to expand the palette of fluorescent dyes that can be employed in the methods described herein. In one embodiment, a first member of a FRET pair is attached to a first tyramide moiety to produce a first labeled tyramide, and a second member of the FRET pair is attached to a second tyramide moiety to produce a second labeled tyramide. In one aspect of the methods described herein, the first and second labeled tyramides are contacted with tyramide-reactive groups of the probes such that both the first and second labeled tyramides are co-localized on the same probe within a sufficient distance to produce the FRET effect. Depending on the distance between adjacent tyramide-reactive groups on the probe, the efficiency of the FRET effect is changed, resulting in higher energy transfer, and therefore a higher ratio of fluorescence from the acceptor and donor dyes for more closely-spaced labeled tyramide FRET pairs and less energy transfer and therefore a lower corresponding fluorescence ratio for less closely spaced FRET pairs. As such, an assay can be multiplexed and evaluated using the same excitatory and emission wavelengths, and the difference in FRET ratio of two probes with different tyramide-reactive group spacing can be achieved, for example by viewing a first emission spectrum in the presence of a first probe, adding the second probe and obtaining a second spectrum that has different relative peak intensities for the two FRET dyes. This would require only one pair of tyramide reagents and fixed excitation and emission wavelengths for all tested probes.

Figure 10:
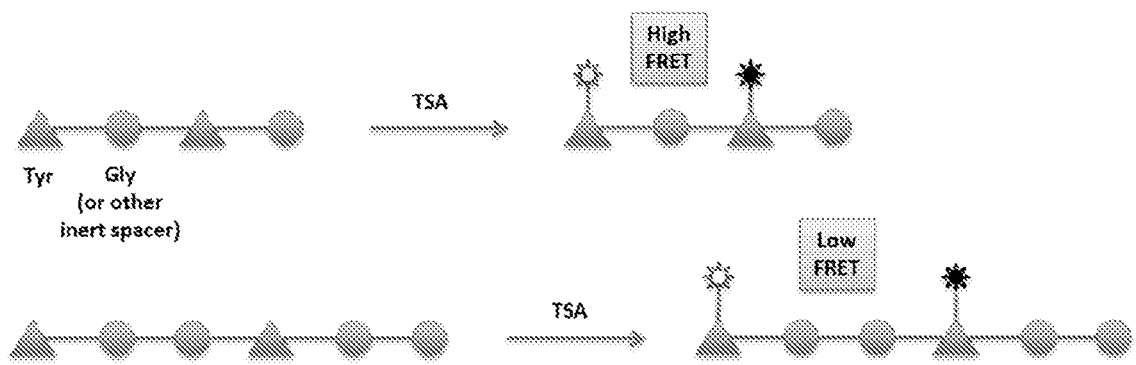
FIG. 10 depicts schematically use of FRET pairs in aspects of the methods described herein.

FIG. 10 provides a scheme taking advantage of varying FRET effects as a factor of spacing of tyramide-reactive groups (e.g., polyphenols) on a tyramide-reactive moiety or tag. The scheme of FIG. 10 illustrates co-labeling of a single poly-phenol tag with two different dyes designed to give FRET. By varying the distance between phenol groups on the tag, different FRET efficiencies should be obtained. This could be read as different ratios of fluorescence intensities for the two dyes, which could be used as the basis for multiplex detection if the different tags are spatially isolated, e.g. on a solid microarray or in a bead library.

FRET requires the overlap of emission spectrum of a first, donor, fluorophore of a FRET pair and the excitation spectrum of a second, acceptor fluorophore of the FRET pair, such that excitation of the first fluorophore of the FRET pair results in excitation of and emission from the second fluorophore of the FRET pair, so long as they are within a sufficient radius of each-other. Distance between members of a FRET pair attenuates the FRET effect such that efficiency of transfer of energy is lowered as distance increases, resulting in lower emission brightness at the emission spectrum of the second flourophore as distance increases. FRET typically works when the effective distance between donor and acceptor is between 10 Å and 100 Å. See, generally, Marras, SAE, "Selection of Fluorophore and Quencher Pairs for Fluorescent Nucleic Acid Hybridization Probes," *Methods in Molecular Biology* 335:3-16 (2006). Thus, as is broadly known in the arts, the donor has an excitation spectrum in a shorter wavelength than the excitation spectrum of the acceptor (they overlap insignificantly, and preferably not at all), the donor has an emission spectrum that significantly overlaps (typically >50%) with the excitation spectrum of the acceptor, and the acceptor emission spectrum is discernable from the donor emission spectrum, and preferably does not overlap. The donor typically has a high extinction coefficient and a high quantum yield. As such one of ordinary skill can select adequate FRET pairs from the multitude of chromophores available commercially. A non-limiting list of examples of common FRET donor/acceptor pairs include: fluorescein isothiocyanate/tetramethylrhodamine isothiocyanate; Cy3/Cy5; Enhanced Green Fluorescent Protein (EGFP)/Cy3; cyan fluorescent protein/yellow fluorescent protein (YFP); and EGFP/YFP.

Activation of the labeled tyramide is achieved by a peroxidase. Although HRP is a traditional, broadly-avalable peroxidase that can be employed in the methods described herein, other enzymes or non-protein catalysts have peroxidase activity and are therefore herein subsumed under the category "peroxidase." The enzyme glutathione peroxidase, and functional mimics thereof are considered useful in activating the tyramide (See, Bhabak, K. P. et al., "Functional Mimics of Glutathione Peroxidase: Bioinspired Synthetic Antioxidants" (2010) *Acc. Chem. Res.* 43(11):1408-1419). Likewise, TAML (tetraamido macrocyclic ligand) catalysts are potentially useful peroxidases in the context of the methods described herein (See, Collins, T. J., "TAML Oxidant Activators: A New Approach to the Activation of Hydrogen Peroxide for Environmentally Significant Problems" (2002) *Acc. Chem. Res.* 35:782-790). Additional peroxidases are disclosed in Day, B. J. ("Catalase and glutathione peroxidase mimics" (2007) *Biochem. Pharmacol.* 77:285-296). An exhaustive database of peroxidase enzymes is the PeroxiBase peroxides database, available on-line. Other compositions with peroxidase activity include graphene, carbon nanotubes and DNA enzymes, which have all shown peroxidase activity and could, in principle, be used in the methods described herein.

In a further embodiment, kits are provided. A kit comprises at a minimum a vessel of any form, which may comprise one or more vessels in the form of compartments. Vessels may be single-use, or contain sufficient contents for multiple uses. A kit also may comprise an array. A kit may optionally comprise one or more additional reagents for use in making or using genetic recognition reagents in any embodiment described herein. The kit comprises a vessel including a selectivity component bound to a plurality of tyramide-binding groups, a selectivity component bound to a peroxidase, or a selectivity component bound to both a peroxidase and a plurality of tyramide-binding groups. Different probes and other reagents are typically packaged into separate vessels, which may be separate compartments in a cartridge for use, e.g., in an automated system.

EXAMPLES

The following examples are for illustrative purposes only.

Example 1

Split-Probe

A split-probe design, as considered by the present invention, includes two or more short probes, which provide better specificity than one long probe, as the shorter probes are less stable in the case of a target mismatch. The terms "mini" or "miniprobe" are used to indicate these shorter split-probe designs.

Figure 11:
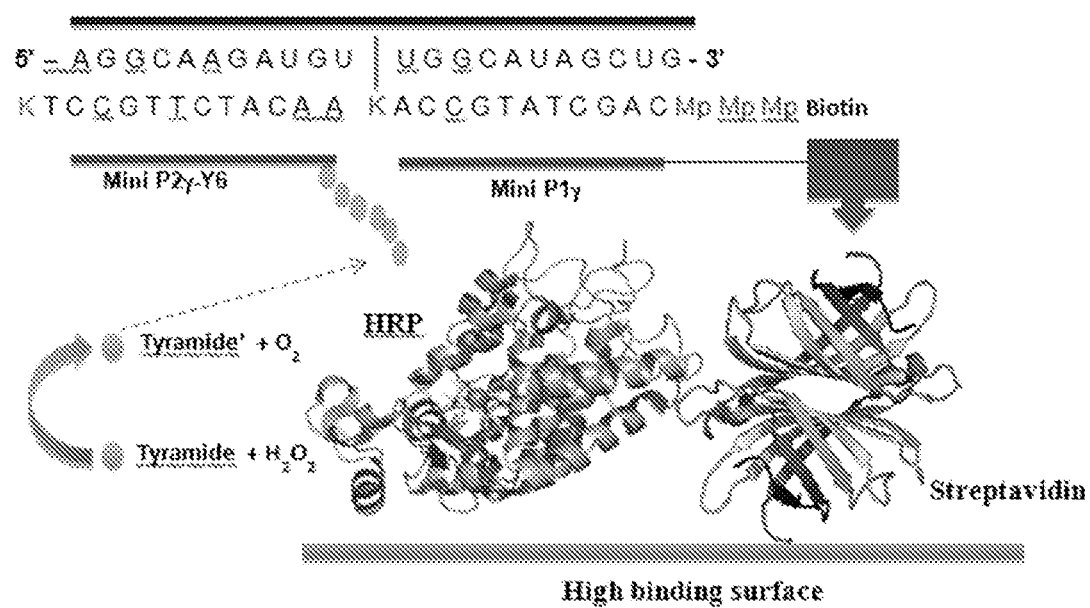
FIG. 11 is a schematic diagram illustrating the split-probe design of Example 1 (SEQ ID NO: 1).

FIG. 11 is a schematic depiction of one embodiment of the present invention. The top of the figure shows the target of the probe, for example a microRNA. The present invention includes a split-probe design. The specific design of the example provided in FIG. 11 designates the split-probe as Mini P2γ-Y6 and Mini P1γ. In this example, the highly reactive tyramide radicals with the Alexa 488 label are covalently conjugated to one or more of the tyrosine residues on the Mini P2γ-Y6 probe, this is a specific example however, and generally any oligomeric or polymeric phenol-containing (hydroxyphenyl-containing) substituent would be useful as a tyramide-binding moiety. The analyte and the probes are mixed together to allow for hybridization between the target and the probes. If the target is present, the probe modified with the oligomeric or polymeric phenol-containing substituent will hybridize with the target. According to one aspect of the present invention, only complete hybridization binds the target to the streptavidin HRP moiety, therefore resulting in an amplified signal by the deposition of Alexa 488 labeled tyramides. The high binding surface indicated in FIG. 11 is a surface, such as a plate or the sides and bottom of a well, on which the detection method is carried out. However, the present invention can also be used to detect DNA or RNA in cells, tissue, or whole organisms in standard in situ hybridization methods.

Example 2

Figure 12:
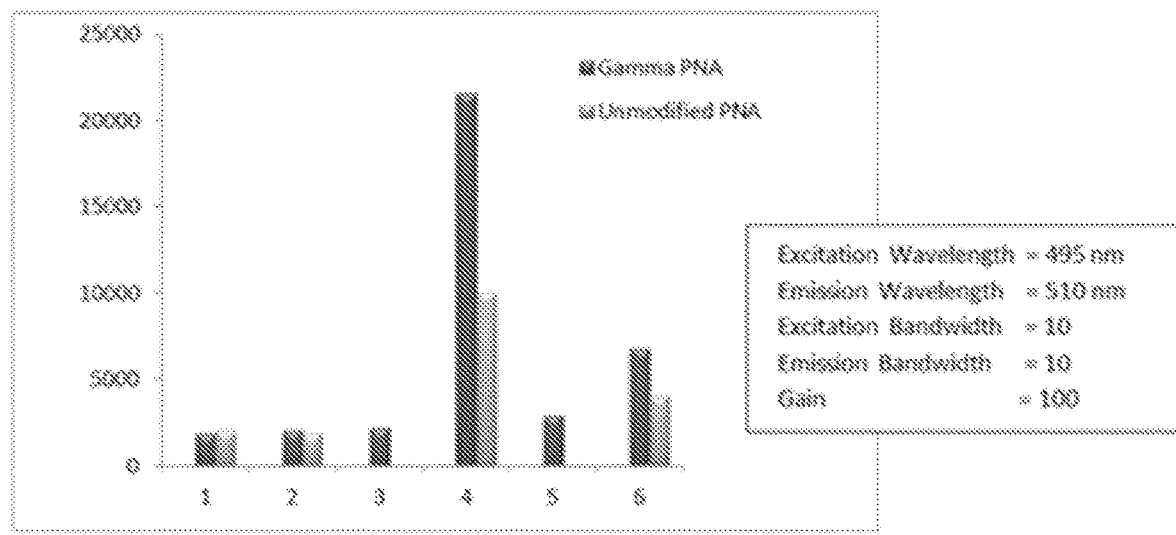
FIG. 12 presents the results of Experiment 1 of the testing of the oligo-tyrosine modified gammaPNA probes of the present invention. The fluorescence signals of both the gammaPNA and the unmodified PNA are reported, wherein: 1. Streptavidin-HRP; 2. Streptavidin-HRP+probe 1+probe 2; 3. Streptavidin-HRP+probe 1+probe 2 (no tyrosines)+target; 4. Streptavidin-HRP+probe 1+probe 2+target; 5. Streptavidin-HRP+probe 1+probe 2 (no tyrosines)+target with a single nucleotide mismatch; and 6. Streptavidin-HRP+probe 1+probe 2+target with mismatch.

The streptavidin-HRP stock solution was prepared by reconstituting the material in 1× PBS buffer. A 100 mM NaHCO$_3$ solution was used to take the pH up to 8.5 for the deposition on to the 96 well plate. 1 μL aliquot of the stock solution was diluted 100 fold using the blocking reagent (1% BSA). 100 μL of this solution was transferred per well and was allowed to sit for 1 hour for the deposition to take place. 12 wells were prepared for the initial study. Each well was washed three times with 1× PBS buffer with Tween to get rid of any unbound streptavidin-HRP. Then the mixtures of the target/mismatch sequence and PNA probes (gamma/unmodified) were added to give 0.8 μM final concentration of each strand to a single well. The strands were allowed to incubate at room temperature for a period of one hour. Three washing steps were performed in order to get rid of any unbound probe/target from the wells. After the washing steps only the biotin containing probe can hold the target or the mismatch sequence on the surface of the well via the streptavidin HRP moiety along with the second probe with tyrosine residues to give a fluorescence signal. After the strands are hybridized and washed a 100 μL aliquot of Alexa 488 labeled tyramide working solution prepared in the amplification buffer consisting with 0.0015% H$_2$O$_2$ was added to each well and allowed for the reaction to take place. After 8 minutes each solution was decanted from each well and three washing steps were performed with 1× PBS to remove any unbound tyramides. The fluorescence signals were measured immediately using the TECAN fluorescence reader (MBIC). The results are summarized in FIG. 12.

Figure 13:
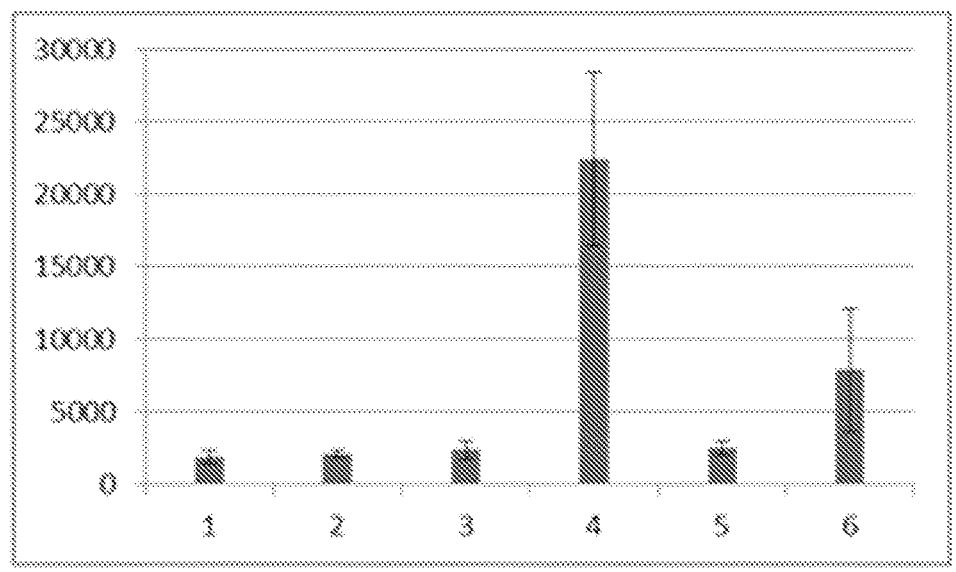
FIG. 13 shows the results for the triplicate evaluation of Experiment 1 for the gammaPNA probes of the present invention, including error bars, wherein: 1. Streptavidin-HRP; 2. Streptavidin-HRP+Mini P1γ+Mini P2γ; 3. Streptavidin-HRP+Mini P1γ+Mini P2γ+target; 4. Streptavidin-HRP+Mini P1γ+Mini P2γ-Y6+target; 5. Streptavidin-HRP+Mini P1γ+Mini P2γ+target with mismatch; and 6. Streptavidin-HRP+Mini P1γ+Mini P2γ-Y6+target with a single nucleotide mismatch.
Figure 14:
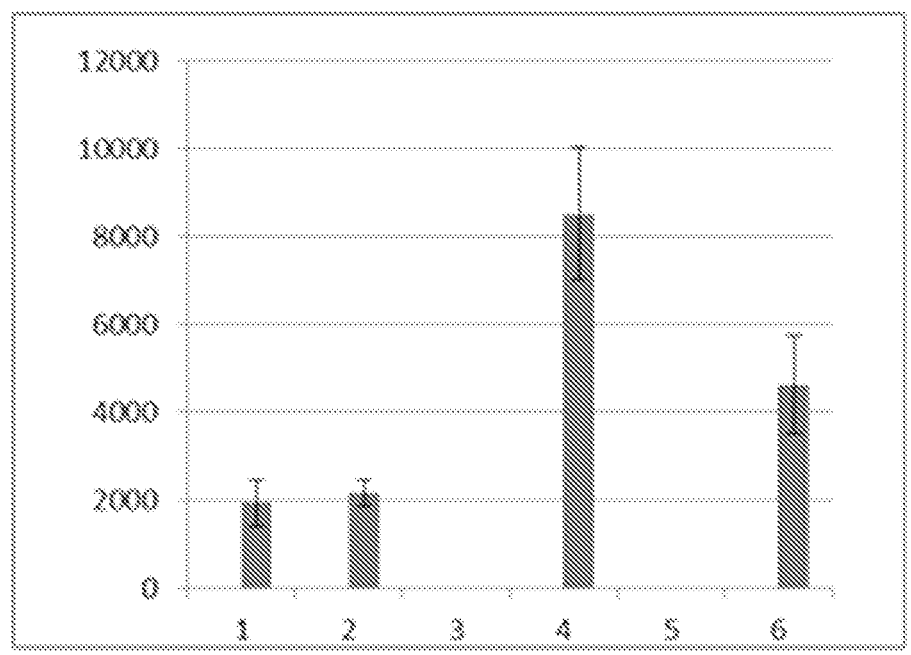
FIG. 14 presents the results for the triplicate evaluation of Experiment 1 for the unmodified PNA probes of the present invention, including error bars, wherein: 1. Streptavidin-HRP; 2. Streptavidin-HRP+Mini P1+Mini P2; 3. –; 4. Streptavidin-HRP+Mini P1+Mini P2-Y6+target; 5. –; and 6. Streptavidin-HRP+Mini P1+Mini P2-Y6+target with a single nucleotide mismatch.

The same experiment was performed in triplicate to evaluate the precision of the signal. The results are summarized, including error bars, in FIGS. 13 and 14.

Example 3

Figure 15:
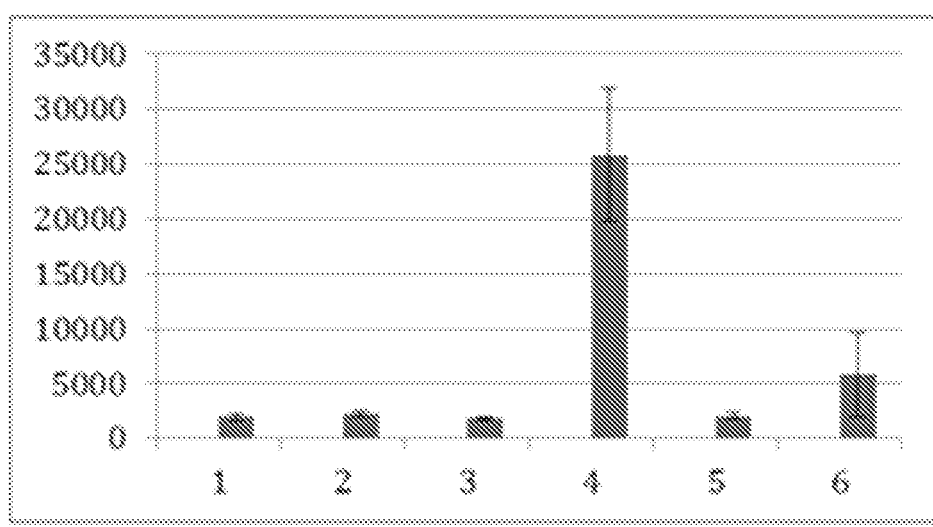
FIG. 15 shows the results for the triplicate evaluation of Experiment 2 for the gammaPNA probes of the present invention, including error bars, wherein: 1. Streptavidin-HRP; 2. Streptavidin-HRP+Mini P1γ+Mini P2γ; 3. Streptavidin-HRP+Mini P1γ+Mini P2γ+target; 4. Streptavidin-HRP+Mini P1γ+Mini P2γ-Y6+target; 5. Streptavidin-HRP+Mini P1γ+Mini P2γ+target with mismatch; and 6. Streptavidin-HRP+Mini P1γ+Mini P2γ-Y6+target with mismatch.
Figure 16:
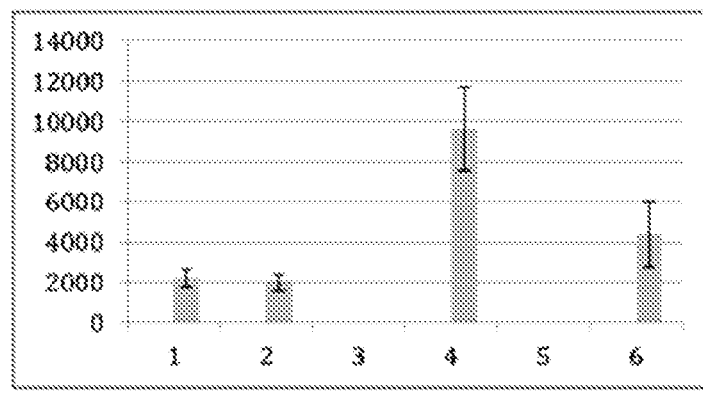
FIG. 16 presents the results for the triplicate evaluation of Experiment 2 for the unmodified PNA probes of the present invention, including error bars, wherein: 1. Streptavidin-HRP; 2. Streptavidin-HRP+Mini P1+Mini P2; 3. –; 4. Streptavidin-HRP+Mini P1+Mini P2-Y6+target; 5. –; and 6. Streptavidin-HRP+Mini P1+Mini P2-Y6+target with mismatch.

In Example 2, the coating of the streptavidin-HRP conjugate to the 96 well plate was performed in a 30-minute time period, but to ensure the complete coating of the wells another experiment was conducted in which the coating was performed overnight in a cold room. Following the exact experimental steps and reagent concentrations after the overnight coating procedure the results were obtained in triplicate to study any difference in the standard deviations calculated. But, as seen in FIGS. 15 and 16, there is no significant deviation from the first set of error bars; therefore it is assumed that the 30-minute coating procedure is adequate.

Example 4

Figure 17:
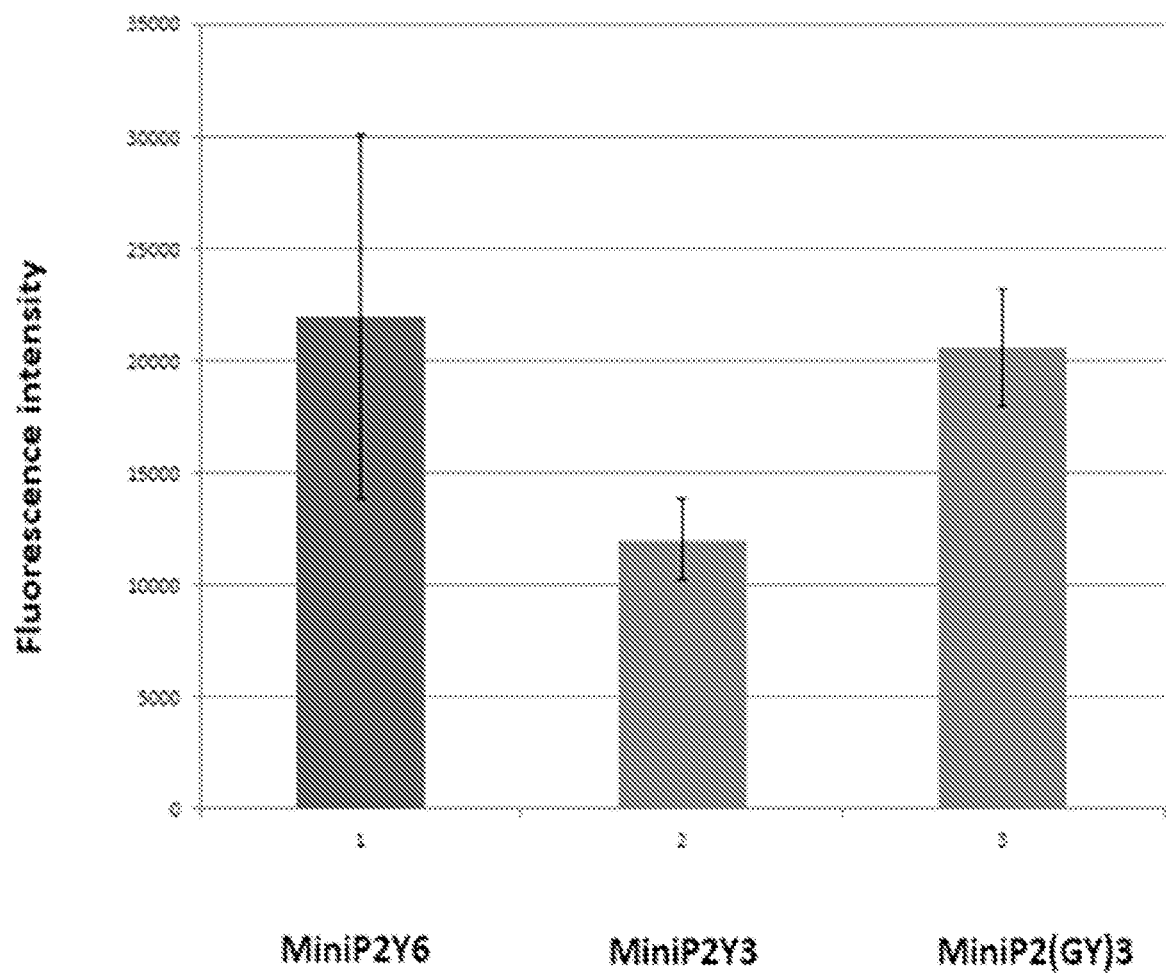
FIG. 17 is a graph comparing the signal from MiniP2Y6, MiniP2Y3 and MiniP2(GY)3.

A comparison was made of the TSA signals generated from three different γPNA probes. The experiment was conducted essentially as described above, with the Mini P2γ-Y6 (MiniP2Y6 in FIG. 17) of FIG. 11 being compared to Mini P2γ-Y3 (Mini P2Y3 in FIG. 17) and Mini P2γ-(GY)3 (Mini P2(GY)3 in FIG. 17). As described above, Mini P2γ-Y6 is a probe comprising six consecutive tyrosine residues. Mini P2γ-Y3 is identical to Mini P2γ-Y6, but contains three consecutive tyrosine residues. Mini P2γ-(GY)3 is identical to Mini P2γ-Y6, but contains an alternating sequence of three tyrosine residues and three glycine residues. The observation that the first and last columns give similar fluorescence (and nearly double that of the middle column) indicates that an improved tag (tyramide-binding moiety) design will have nonconsecutive tyrosines (or phenol groups). It is believed, without any intent of being bound by that theory, that self-quenching occurs between dyes that are deposited too close to one another.

The following outlines various aspects of the invention described herein.

1. A method of identifying the presence of a target analyte in a sample, comprising:
    a. forming a complex of a selectivity component specific to the target analyte with the target analyte in the sample, a peroxidase, such as horseradish peroxidase, and a tag comprising a plurality of tyramide-binding groups;
    b. contacting the peroxidase with labeled tyramide, forming labeled tyramide radicals, that link to the tyramide-binding groups of the tag; and
    c. detecting the linkage of the label to the complex, such as by fluorescent microscopy, spectroscopy, flow cytometry, and/or imaging techniques.
2. The method of paragraph 1, in which the selectivity component is a nucleic acid or a nucleic acid analog, and binds selectively to a nucleic acid target analyte by hybridization.
3. The method of either of paragraphs 1 and 2, in which the selectivity component is a γPNA comprising residues of gamma-modified N-(2-aminoethyl)glycine monomers of the following structure:

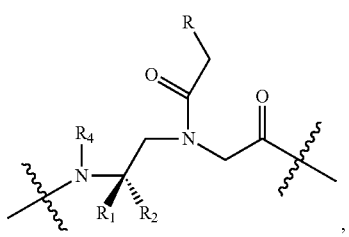

(I)

where R1, R2 and R4 are, independently, H, amino acid side chains, linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$ cycloalkyl, $(C_3-C_8)$aryl$(C_1-C_6)$alkylene, $(C_3-C_8)$cycloalkyl $(C_1-C_6)$alkylene, PEGylated moieties of the preceding comprising from 1 to 50 $(-O-CH_2-CH_2-)$ residues, $-CH_2-(OCH_2-CH_2)_q OP_1$, $-CH_2-(OCH_2-CH_2)_q-NHP_1$, $-CH_2-(OCH_2-CH_2-O)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S-[CH_2CH_2]_s NHC(NH)NH_2$, where $P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl $(C_1-C_6)$alkylene and $(C_3-C_8)$cycloalkyl$(C_1-C_6)$alkylene; q is an integer from 0 to 10, inclusive; r and s are each independently integers from 1 to 50, inclusive, or a tyramide-binding group, such as a hydroxyphenyl group, where R1 and R2 are different, and R is a nucleobase.

4. The method of paragraph 3, wherein one of R1 and R2 are H.
5. The method of either of paragraphs 3 and 4, wherein at least one of R1, R2 and R4 comprise a hydroxyphenyl group.
6. The method of paragraph 2, in which the nucleic acid or nucleic acid analog selectivity component comprises:
   a. a first probe comprising a sequence complementary to a first target sequence of the nucleic acid target analyte, and a second probe complementary to a second target sequence of the nucleic acid target analyte, wherein the peroxidase is bound to the first probe and the tag is bound to the second probe; or
   b. a probe comprising a sequence complementary to a target sequence of the nucleic acid target analyte and bound to the peroxidase and the tag.
7. The method of any of paragraphs 1-6, in which the peroxidase or the tag is immobilized on substrate.
8. The method of any of paragraphs 1-7, in which selectivity components having different target analyte specificities are arranged in an array, such as on a substrate, a plurality of beads, or a multiwall plate.
9. The method of any of paragraphs 1-8, in which the target analyte is affixed to a microscope slide.
10. The method of any of paragraphs 1-8, in which the method is multiplexed by forming a second complex with a second selectivity reagent specific to a second target analyte different from the target analyte, and detecting binding of the second selectivity reagent to the second target analyte using a second labeled tyramide that can be the same as the labeled tyramide.
11. The method of paragraph 1, wherein the selectivity component is a binding reagent, antibody or aptamer.
12. The method of any of paragraphs 1-11, in which the tag is a polypeptide, a PNA or a γPNA having three or more pendant tyramide-binding groups, such as hydroxyphenyl groups.
13. The method of paragraph 9, in which the tag is a polypeptide of from three to 25 amino acids, comprising three or more tyrosine residues.
14. The method of paragraph 9, in which the tag is a polypeptide, a PNA or a γPNA comprising three or more tyramide-binding groups separated from each-other by at least one amino acid, PNA, or γPNA residue that does not comprise a tyramide-binding group.
15. The method of any of paragraphs 1-10 and 12-14, in which the target analyte is a microRNA.
16. A kit comprising, independently in one or more vessels:
   a. a selectivity component specific to a target analyte bound, for example covalently, to one of a tag comprising a plurality of tyramide-binding groups or a peroxidase,
   b. the other of the tag or peroxidase bound, e.g., covalently attached, to either the selectivity reagent or to a probe or a binding agent that either selectively binds the target analyte or binds to a complex formed between the selectivity component and the target analyte; and
   c. a labeled tyramide, preferably labeled with a fluorophore.
17. A binding reagent for use in a tyramide signal amplification assay comprising a selectivity component covalently linked to a plurality of tyramide-binding groups.
18. The binding reagent of either of paragraphs 16 and 17, in which the selectivity component is a nucleic acid or a nucleic acid analog.
19. The binding reagent of either of paragraphs 16 and 17, in which the selectivity component is a peptide nucleic acid.
20. The binding reagent of either of paragraphs 16 and 17, in which the selectivity component is an antibody, an aptamer, a ligand, or an engineered polypeptide.
21. The binding reagent of any one of paragraphs 16-20, in which the tyramide-reactive group is a hydroxyphenyl group.
22. The binding reagent of any one of paragraphs 16-20, comprising a tyramide-reactive moiety covalently-linked to the selectivity component.
23. The binding reagent of paragraph 19, in which the tyramide-reactive moiety is a polymer comprising one or more tyramide-reactive groups.
24. The binding reagent of paragraph 23, in which the tyramide-reactive moiety is a γPNA comprising γPNA residues of from 1 to 20 residues in length and having a plurality of pendant tyramide-reactive groups.
25. The binding reagent of paragraph 24, in which at least one γPNA residue of the γPNA comprising a pendant tyramide-reactive group is separated from other γPNA residues comprising a pendant tyramide-reactive group by at least one γPNA residue that does not have a tyramide-reactive group.
26. The binding reagent of paragraph 16, in which the selectivity component is a gamma peptide nucleic acid (γPNA).
27. The binding reagent of paragraph 16, in which the tyramide-reactive moiety is an oligopeptide of up to 25 amino acid residues, comprising a plurality of tyrosine residues.
28. The binding reagent of paragraph 27, in which the tyrosine residues are separated from other tyrosine residues in the tyramide-reactive moiety by at least one different amino acid residue that is not tyrosine, preferably glycine.

29. The binding reagent of paragraph 16, covalently linked to a peroxidase enzyme, such as horseradish peroxidase.

Having described this invention, it will be understood to those of ordinary skill in the art that the same can be performed within a wide and equivalent range of conditions, formulations and other parameters without affecting the scope of the invention or any embodiment thereof.

We claim:

1. A method of identifying the presence of a target analyte in a sample, comprising:
   a. forming a complex of a first selectivity component, specific to the target analyte, with the target analyte in the sample, a peroxidase, and a tag comprising a plurality of tyramide-binding groups,
   wherein:
   (i) the tag and the peroxidase are both linked to the first selectivity component;
   (ii) one of the peroxidase and tag is linked to the first selectivity component and the other of the peroxidase and tag is linked to an additional selectivity component that binds specifically to either the first selectivity component or to the target analyte; or
   (iii) the peroxidase and tag are both linked to one or more additional selectivity components that bind specifically to the first selectivity component;
   b. contacting the peroxidase with labeled tyramide, forming labeled tyramide radicals, that link to the tyramide-binding groups of the tag; and
   c. detecting the linkage of the label to the tag.

2. The method of claim 1, in which the first selectivity component is a nucleic acid or a nucleic acid analog, and binds selectively to a nucleic acid target analyte by hybridization.

3. The method of claim 2, in which the first selectivity component is a γPNA comprising residues of gamma-modified N-(2-aminoethyl)glycine monomers of the following structure:

(I)

where R1, R2 and R4 are, independently, H, amino acid side chains, linear or branched $(C_1\text{-}C_8)$alkyl, $(C_2\text{-}C_8)$alkenyl, $(C_2\text{-}C_8)$alkynyl, $(C_1\text{-}C_8)$hydroxyalkyl, $(C_3\text{-}C_8)$aryl, $(C_3\text{-}C_8)$cycloalkyl, $(C_3\text{-}C_8)$aryl$(C_1\text{-}C_6)$alkylene, $(C_3\text{-}C_8)$cycloalkyl$(C_1\text{-}C_6)$alkylene, PEGylated moieties of the preceding comprising from 1 to 50 (—O—$CH_2$—$CH_2$—) residues, —$CH_2$—($OCH_2$—$CH_2$)$_q$$OP_1$, —$CH_2$—($OCH_2$—$CH_2$)$_q$—$NHP_1$, —$CH_2$—($OCH_2$—$CH_2$—O)$_q$—$SP_1$ and —$CH_2$—($SCH_2$—$CH_2$)$_q$—$SP_1$, —$CH_2$—($OCH_2$—$CH_2$)$_r$—OH, —$CH_2$—($OCH_2$—$CH_2$)$_r$—$NH_2$, —$CH_2$—($OCH_2$—$CH_2$)$_r$—NHC(NH)$NH_2$, or —$CH_2$—($OCH_2$—$CH_2$)$_r$—S—S[$CH_2CH_2$]$_s$NHC(NH)$NH_2$, where $P_1$ is selected from the group consisting of H, $(C_1\text{-}C_8)$alkyl, $(C_2\text{-}C_8)$alkenyl, $(C_2\text{-}C_8)$alkynyl, $(C_3\text{-}C_8)$aryl, $(C_3\text{-}C_8)$cycloalkyl, $(C_3\text{-}C_8)$aryl$(C_1\text{-}C_6)$alkylene and $(C_3\text{-}C_8)$cycloalkyl$(C_1\text{-}C_6)$alkylene; q is an integer from 0 to 10, inclusive; r and s are each independently integers from 1 to 50, inclusive, or a tyramide-binding group, such as a hydroxyphenyl group, where R1 and R2 are different, and R is a nucleobase.

4. The method of claim 3, wherein at least one of R1, R2 and R4 comprises a hydroxyphenyl group.

5. The method of claim 2, in which the nucleic acid or nucleic acid analog selectivity component comprises:
   a. a first probe comprising a sequence complementary to a first target sequence of the nucleic acid target analyte, and a second probe complementary to a second target sequence of the nucleic acid target analyte, wherein the peroxidase is bound to the first probe and the tag is bound to the second probe; or
   b. a probe comprising a sequence complementary to a target sequence of the nucleic acid target analyte and bound to the peroxidase and the tag.

6. The method of claim 1, in which selectivity components having different target analyte specificities are arranged in an array.

7. The method of claim 1, in which the method is multiplexed by forming a second complex with a second selectivity reagent specific to a second target analyte different from the target analyte, and detecting binding of the second selectivity reagent to the second target analyte using a second labeled tyramide that can be the same as the labeled tyramide.

8. The method of claim 1, wherein the first selectivity component is a binding reagent, antibody or aptamer.

9. The method of claim 1, wherein the tag is a polypeptide, a PNA or a γPNA having three or more pendant tyramide-binding groups.

10. The method of claim 1, wherein the tag is a polypeptide of from three to 25 amino acids, comprising three or more tyrosine residues.

11. A kit comprising, independently in one or more vessels:
   a. a first selectivity component specific to a target analyte a tag comprising a plurality of tyramide-binding groups, and a peroxidase,
   b. wherein:
   (i) the tag and the peroxidase are both linked to the first selectivity component;
   (ii) one of the peroxidase and tag is linked to the first selectivity component and the other of the peroxidase and tag is linked to an additional selectivity component that binds specifically to either the first selectivity component or to the target analyte; or
   (iii) the peroxidase and tag are both linked to one or more additional selectivity components that bind specifically to the first selectivity component; and
   c. a labeled tyramide.

12. A binding reagent for use in a tyramide signal amplification assay comprising a selectivity component covalently linked to a plurality of tyramide-binding groups.

13. The binding reagent of claim 12, wherein the first selectivity component is a nucleic acid or a nucleic acid analog.

14. The binding reagent of claim 12, wherein the first selectivity component is a peptide nucleic acid.

15. The binding reagent of claim 12, comprising a tyramide-reactive moiety covalently-linked to the first selectivity component.

16. The binding reagent of claim 15, wherein the tyramide-reactive moiety is a polymer comprising one or more tyramide-reactive groups.

17. The binding reagent of claim 16, in which the tyramide-reactive moiety is a γPNA comprising γPNA residues of from 1 to 20 residues in length and having a plurality of pendant tyramide-reactive groups.

18. The binding reagent of claim 12, wherein the first selectivity component is a gamma peptide nucleic acid (γPNA).

19. The binding reagent of claim 12, wherein the tyramide-reactive moiety is an oligopeptide of up to 25 amino acid residues, comprising a plurality of tyrosine residues.

20. The binding reagent of claim 12, covalently linked to a peroxidase enzyme.

21. The method of claim 1, wherein the peroxidase is horseradish peroxidase or the linkage of the label to the tag is detected by fluorescent microscopy, spectroscopy, flow cytometry, or imaging techniques.

22. The method of claim 1, wherein the tyramide-binding group is a hydroxyphenyl group.

23. The method of claim 1, wherein the peroxidase is linked to the first selectivity component and the tag is linked to a second selectivity component, and wherein the first and second selectivity components are nucleic acid or nucleic acid analog probes that bind specifically to the target analyte.

24. The method of claim 1, wherein the peroxidase is linked to the first selectivity component through a binding pair and the tag is linked to a second selectivity component, and wherein the first and second selectivity components are nucleic acid or nucleic acid analog probes that bind specifically to the target analyte.

25. The method of claim 1, wherein the tag and peroxidase are bound covalently to the first selectivity component, and wherein the first selectivity component comprises a nucleic acid, nucleic acid analog, nucleic acid ligand, or aptamer.

26. The method of claim 1, wherein the first selectivity component comprises an antibody covalently linked to a first nucleic acid or nucleic acid analog comprising a target sequence that hybridizes with a second nucleic acid or nucleic acid analog linked to a tag and a peroxidase and comprising a sequence complementary to the target sequence of the first nucleic acid or nucleic acid analog.

27. The method of claim 1, wherein the first selectivity component comprises an antibody covalently linked to a first nucleic acid or nucleic acid analog comprising a target sequence that hybridizes with a second nucleic acid or nucleic acid analog linked to a tag and third nucleic acid or nucleic acid analog linked to a peroxidase, the second and third nucleic acid or nucleic acid analog comprising non-overlapping sequences complementary to the target sequence of the first nucleic acid or nucleic acid analog.

28. The method of claim 1, wherein the first selectivity component comprises an antibody linked to the tag or peroxidase, and the other of the peroxidase and tag is linked to a second antibody that binds specifically to the first selectivity component.

* * * * *

UNITED STATES PATENT AND TRADEMARK OFFICE
CERTIFICATE OF CORRECTION

| | |
|---|---|
| PATENT NO. | : 11,124,822 B2 |
| APPLICATION NO. | : 15/518811 |
| DATED | : September 21, 2021 |
| INVENTOR(S) | : Bruce Alan Armitage et al. |

It is certified that error appears in the above-identified patent and that said Letters Patent is hereby corrected as shown below:

In the Claims

Column 32, Line 34, Claim 3, before "where" delete "such as a hydroxyphenyl group,"

Column 33, Line 3, Claim 11, delete "analyte" and insert -- analyte, --

Signed and Sealed this
Twenty-fifth Day of April, 2023

*Katherine Kelly Vidal*

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 22
<212> TYPE: RNA
<213> ORGANISM: Artificial sequence
<220> FEATURE:
<223> OTHER INFORMATION: Target RNA sequence

<400> SEQUENCE: 1
aggcaagaug uuggcauagc ug                22